(12) United States Patent
Wu et al.

(10) Patent No.: US 11,506,657 B2
(45) Date of Patent: Nov. 22, 2022

(54) DETECTION DEVICE

(71) Applicant: Hangzhou Biotest Biotech Co., LTD., Zhejiang (CN)

(72) Inventors: Shujiang Wu, Zhejiang (CN); John Wu, San Diego, CA (US); Liang Hong, Zhejiang (CN); Yangyu Zhu, San Diego, CA (US)

(73) Assignee: HANGZHOU BIOTEST BIOTECH CO., LTD., Hangzhou (CN)

( * ) Notice: Subject to any disclaimer, the term of this patent is extended or adjusted under 35 U.S.C. 154(b) by 180 days.

(21) Appl. No.: 16/942,041

(22) Filed: Jul. 29, 2020

(65) Prior Publication Data

US 2021/0033598 A1 Feb. 4, 2021

Related U.S. Application Data

(60) Provisional application No. 62/881,546, filed on Aug. 1, 2019.

(30) Foreign Application Priority Data

Aug. 1, 2019 (CN) .......................... 201910705504.6

(51) Int. Cl.
*G01N 33/52* (2006.01)
*G01N 21/78* (2006.01)
*B01L 3/00* (2006.01)

(52) U.S. Cl.
CPC .......... *G01N 33/521* (2013.01); *B01L 3/5023* (2013.01); *G01N 21/78* (2013.01); *B01L 2300/0832* (2013.01); *B01L 2300/123* (2013.01); *B01L 2300/168* (2013.01)

(58) Field of Classification Search
CPC .... G01N 33/521; G01N 21/78; B01L 3/5023; B01L 2300/123; B01L 2300/168; A61B 2010/0006
See application file for complete search history.

(56) References Cited

U.S. PATENT DOCUMENTS

| | | | | |
|---|---|---|---|---|
| 2,332,137 A | * | 10/1943 | Gurley | B65D 75/26 524/21 |
| 2,987,174 A | * | 6/1961 | Free | B01L 3/545 206/204 |
| 7,244,392 B1 | * | 7/2007 | Konecke | B01L 3/502 436/166 |
| 9,784,733 B1 | * | 10/2017 | Wang | G01N 21/78 |
| 2003/0021726 A1 | * | 1/2003 | Wu | B01L 3/502 422/404 |

(Continued)

*Primary Examiner* — Jennifer Wecker
*Assistant Examiner* — Alea N. Martin
(74) *Attorney, Agent, or Firm* — NZ Carr Law Office

(57) ABSTRACT

The present invention provides a detection device comprises a testing element and a transparent area, wherein the testing element comprises a detection area which is configured to detect a presence of an analyte in a liquid sample; the transparent area is configured to read the test result on the detection area through the transparent area; a part of the transparent area contacts a part of the detection area, or the detection area and the transparent area are arranged in one sealed space, thus to make the air in the sealed space not exchange with the air outside the sealed space; the scheme can reduce the mist to ensure the test result is displayed clearly.

20 Claims, 11 Drawing Sheets

(56) References Cited

U.S. PATENT DOCUMENTS

| | | | |
|---|---|---|---|
| 2003/0099572 A1* | 5/2003 | Ng | B01L 3/508 422/417 |
| 2011/0107824 A1* | 5/2011 | Lv | A61B 10/0045 73/64.56 |

* cited by examiner

DETECTION DEVICE

CROSS REFERENCE OF THE RELATED APPLICATION

The present application claims the benefit of Chinese Patent Application No. 2019107055046, filed on Aug. 1, 2019, and U.S. patent Application No. 62/881,546, filed on Aug. 1, 2019. The content of these applications including all tables, diagrams and claims is incorporated hereby as reference in its entirety.

TECHNICAL FIELD

The present invention relates to a collection and detection device, in particular to a device for collecting and detecting a presence of an analyte in a liquid sample in the field of rapid diagnosis.

BACKGROUND ART

The following background art information is only a general introduction of the background and will not constitute any restrictions on the present invention.

A medical or household rapid detection device is generally used to detect a presence of an analyte in a sample, for example, for pregnancy test, drug detection, etc. The detection device is generally provided with a collecting chamber for collecting a sample to be tested (some do not have a liquid sample collecting chamber), and a testing element is installed in the collecting chamber. The sample to be tested enters into the collecting chamber through an opening of the collecting chamber and contacts the testing element, so that the testing element detects the sample to be tested. The testing element has a detection area for displaying a test result, and the test result can be read from outside the collecting chamber through the side wall of the collecting chamber. Generally, a part of the collecting chamber is transparent, and the result on the detection area is read through the transparent part. In some cases, the testing element does not read the test result immediately after detecting the sample collected in the collecting chamber, but sends it to the testing agency in batches for scanning and reading by a mechanical electronic device. Therefore, the detection device also comprises a cover body which fits with the collecting chamber to form a sealed chamber, and the sample and the testing element are sealed in the collecting chamber, thereby preventing the sample from being contaminated by the outside or the sample from being spilled or leaking from the collecting chamber during the transportation and transfer process.

Additionally, the testing element is generally located in a casing, within an area where the detection area of the testing element corresponds to the casing (the area of the casing is generally made of a transparent plastic or thin film), the detection area of the testing element is read through the transparent area of the casing, especially the color of the test line is used to judge whether the test result is positive or negative.

After detecting a sample, due to influence of certain factors, the existing collection and detection device may not be able to accurately read the test result on the testing element from outside the collecting chamber or the corresponding casing of the detection area. Hence, it is required to design and improve the traditional detection device to increase the convenience in using the detection device and the accuracy when reading the test result.

DETAILED DESCRIPTIONS OF THE INVENTION

The invention relates to a collection and detection device, and the device has the advantages that it has simple structure and is convenient to manufacture, and can read the test result on the testing element from outside the collecting chamber clearly, quickly and conveniently without being affected by the external environment or the internal environment of the device.

In one aspect, the present invention provides a detection device, and the device comprises a testing element, wherein the testing element comprises a detection area used for detecting a presence of an analyte in a liquid sample; and a transparent area through which the test result on the detection area can be read, and the detection area covers the surface of the transparent area, or the surface of the detection area fits together with that of the transparent area. In some embodiments, the prevent invention comprises a casing for containing a testing element, the casing has a transparent area and the test result on the detection area can be read through the transparent area. In this way, small droplets are form on the surface of the transparent area during testing so that no fog is generated in the transparent area, and the test result on the detection area can be read clearly. In some embodiments, the detection area of the testing element includes an absorbent material, and a liquid sample flows through the absorbent material. In some embodiments, the detection area includes a substance for detection which can directly detect a presence of any an analyte in a test sample. In some embodiments, a presence or absence of other analytes is indicated by a marker substance, and the said marker substance is a colored marker substance which can be read by naked eyes; while in some other embodiments, the so-called reading includes reading by an electronic device, for example, reading by a scanner or a fluorescent reading device.

The substantial contact herein covers a short distance, which makes the absorbent material of the detection area partially contacts the transparent part so as to contact the small droplets on the transparent part and make the droplets disappear from the transparent part (the absorbent material absorbs the droplets on the transparent area), and reduce the coverage of droplets, so that the transparent part is substantially free of droplets and becomes more transparent, thus to display the detection area more clearly. The contact may be direct contact or indirect contact. The so-called indirect contact means that the transparent area may present a multilayer structure. If the area where small droplets are formed is in some areas of a multilayer structure, when the detection area contacts this area, the effect of "atomizing" is reduced. Of course, the detection area does not necessarily contact the above area, and the contact of that area with other absorbent materials that can absorb small droplets is allowed; in some embodiments, these absorbent materials are transparent, and a test result on the detection area can be read through the transparent absorbent materials.

In addition, the contact may be a substantial contact of the full detection area with the transparent area, or a substantial contact of a part of the detection area with a part of the transparent area. In some embodiments, the area containing a test line on the detection area is in substantial contact with a part of the transparent area. In some embodiments, a result control area is arranged on the upstream of the detection area, and the control area or a part of the control area is in substantial contact with a part of the transparent area.

The detection area of the testing element is enabled to directly or indirectly contact with the transparent area for reading the test result of the detection area through a transparent part on the casing, thereby reducing the condensed droplets on the transparent part and facilitating reading of the test result. This is an embodiment easy to implement. Small droplets on the surface of the transparent area is generally generated due to a temperature difference between the ambient temperature and the transparent area itself, the droplets condensed in the transparent area (generally made of a plastic material) are formed when the water vapors in the environment encounter the transparent area as the ambient temperature is higher than the transparent area itself or its surface. Or, after the detection device receives a droplet sample or collects a liquid sample, the temperature of the liquid sample itself is higher than that of the transparent area, or the temperature of the liquid sample is higher than the ambient temperature, so that the liquid sample evaporates water vapor and encounters the transparent area (with the temperature being lower than that of the vapor) and then condense into droplets covering the surface of the transparent area, thereby forming a surface similar to "an atomized one". Hence, the test result on the detection area, is not read inaccurately.

In some embodiments, the detection device comprises a blocking element, which can reduce or block the fluid exchange between the area between the detection area and the transparent area and the surrounding area. In some embodiments, the fluid is a gas and/or a liquid, or a mixture of a gas and a liquid, or a water vapor. The blocking element makes the detection area contact with the transparent area or cover the transparent area to reduce the exchange of a water vapor or water steam, or block the exchange of a water vapor between the contacted areas with the outside. The transparent area is used for reading the test result on the detection area through a transparent part. The reading can be achieved by naked eyes or a machine. The machine reads the test result by taking a picture and scanning.

In some embodiments, the detection area does not necessarily need to substantially contact with the transparent area. At this time, the detection area and the transparent area are located in a relatively sealed space so that the sealed space does not substantially exchange water vapor with the area outside the space, and the fluid therein is generally a gas containing water vapor. In some embodiments, the water vapor can condense into droplets in the transparent area. In this way, the water vapor from the outside does not enter into the sealed space containing the detection area and the transparent area, which will reduce the entry of water vapor in the space, thereby further reducing the formation of water vapor in the sealed space into small droplets on the surface of the transparent area. In some embodiments, the sealing can be achieved by a blocking element.

It can also be understood that the detection area covers the transparent area, and no space is reserved between the detection area and the transparent area. This is special situation when the detection area and the transparent area are considered in a sealed space.

In some embodiments, the transparent area is located on a side wall of a liquid collecting device, the collecting device comprises a chamber for collecting a fluid sample, and the transparent area is located on a wall of the collecting chamber. Therefore, in some embodiments, when the testing element is combined with the collecting chamber, the area between the detection area and the side wall of the collecting chamber is in a sealed state or the detection area contacts with the side wall of the collecting chamber, or the detection area covers on the side wall of the collecting device. Preferably, when the testing element is combined with the collecting chamber, the area between the detection area and the inner wall of the collecting chamber is liquid-sealed. This reduces the vapors outside from entering into the inner wall of the collecting chamber facing the detection area.

In some preferred embodiments, further, the blocking element makes the detection area attach to the side wall of the collecting chamber; and allows the detection area to have a substantially indirect contact with a part of the transparent area on the collecting chamber. Or, the blocking element can fill up the area between the detection area and the side wall of the collecting chamber; the blocking element herein can be located between the collecting chamber and the detection area, and at this time, the blocking element may also be transparent, and in this case, the blocking element is in substantial contact with the detection area. The attaching therein is a connected state, indicating that the detection area and the blocking element are in contact connection.

In some embodiments, the testing element is located in a groove of a carrier, and the carrier is configured on a side wall of a chamber, at this time, the side of the carrier with a testing element is enabled to substantially contact with a side wall of the collecting chamber; or, the detection area of the testing element in the carrier is made in substantial contact with the side wall of the chamber. When a testing element is arranged in the groove of the carrier, the testing element is sealed in the groove of the carrier, or the detection area of the testing element is located in the groove of the carrier, and the carrier is arranged on the side wall of the chamber, at this time, a transparent part of the groove can be used to read the test result on the detection area; and in order to read the test result, the test result has to be read through the transparent part on the side wall of the chamber and the transparent part on the groove; in this case, it is expected that the side (outside) of the transparent part on the groove of the carrier directly contact with the side wall of the chamber, and also that the detection area directly contacts with the other side of the transparent part of the groove (directly facing the detection area), or choose either one of the two. This reduces the formation of small droplets in the transparent part of the groove and the side walls of the chamber, thereby covering the transparent surface.

Similarly, the transparent part of the groove and the detection area form a substantially sealed space, thereby reducing the exchange of water vapors with the outside. Optionally, a substantially sealed space is formed between the transparent part of the groove and the side wall of the chamber, thereby reducing the formation of small droplets between the transparent part of the groove and the side wall of the chamber.

In some embodiments, the transparent area presents a plane structure, or a sidewall part of the collecting chamber presents a plane structure, so that the plane structure easily contacts or covers the detection area.

In some embodiments, the blocking element may be a raised structure, the raised structure being located in the groove of the carrier and the raised structure contacting the back side of the detection area of the testing element. When the carrier contacts the side wall of the chamber, the raised structure makes the detection area attach to the side wall surface of the chamber. The side wall is transparent and used to read the test result on the detection area through a transparent area.

In some other embodiments, further, when the testing element is combined with the collecting chamber, the detection area of the testing element is arranged between the blocking element and an inner wall of the collecting chamber.

Further, the blocking element comprises a clamping area for fitting the inner wall of the collecting chamber and clamping the detection area; when the testing element is combined with the collecting chamber, the detection area is clamped between the clamping area and the inner wall of the collecting chamber. The clamping area herein may comprise a raised structure.

Further, when the testing element is combined with the collecting chamber, the clamping area covers the back of the detection area and the clamping area attaches to the back of the detection area, in this way, the clamping area can make the detection area and the side wall of the collecting chamber fit tightly together. Preferably, there is one clamping area, and the clamping area collectively covers the back of the detection area of a plurality of testing elements; or, there may be two or more clamping areas, and each clamping area covers the back of one, two or more detection areas. Preferably, the blocking element is also a part of the carrier of the testing element, the carrier of the testing element has a groove for accommodating the testing element, and the clamping area may be a bottom face of the groove; or, the clamping area is a bump arranged in the groove. In this way, the bump of the groove makes the detection area of the testing element and the surface of the carrier substantially in the same level, so that when the carrier is close to the side wall of the collecting chamber, the detection area of the testing element can be closely attached to the side wall, thus to reduce the formation of mists from the vapors outside on the attached side wall. The detection area is closely attached to the transparent side wall, which blocks vapors outside from condensing into small droplets in the attached area. Even if there is a liquid flowing through the detection area, and it produces small droplets in the attached area, and the droplets will be absorbed by the detection area containing water-absorbent material.

Further, the inner wall of the collecting chamber has a attaching area for attaching surface the detection area and the attaching area covers the detection area; when the testing element is combined with the collecting chamber, the detection area is clamped between the clamping area and the attaching area. Preferably, when the testing element is combined with the collecting chamber, the clamping area is aligned with the attaching area. Preferably, the attaching area is a partial area of the inner wall of the collecting chamber; or, the attaching area is a bulge arranged on the inner wall of the collecting chamber. Preferably, there is one attaching area, and the attaching area covers all the detection areas; or, there are two or more attaching areas, and each attaching area covers one, two, or more detection areas. In some embodiments, the attaching area of the inner wall of the collecting chamber adopts a plane or slab structure. The attaching area may also be a raised structure on the side wall, and the raised structure is transparent.

Further, the clamping area has a clamping surface for contacting the back of the detection area, and the attaching area has a attaching surface for contacting the detection area; when the testing element is combined with the collecting chamber, the clamping surface is parallel to the attaching surface. Preferably, the attaching surface and the clamping surface are of a plane surface, a curved surface, a cylindrical surface or a conical cylindrical surface.

Further, when the testing element is combined with the collecting chamber, the distance between the attaching surface and the clamping surface is less than or equal to the thickness of the detection area. Thickness of the detection area means the thickness of the area where the detection area of the testing element is located. Preferably, when the testing element is combined with the collecting chamber, the distance between the attaching surface and the clamping surface is greater than zero, so that the surface displaying the test result on the detection area can be closely attached to the attaching surface.

In other embodiments, when the testing element is combined with the collecting chamber, the blocking element is located between the detection area and the inner wall of the collecting chamber, and the detection area gets close to the blocking element relative to the back of the detection area. Preferably, the blocking element is made of a transparent or a translucent material. Preferably, the blocking element is fixedly connected or detachably connected to the detection area. Preferably, the blocking element is detachably connected to the inner wall of the collecting chamber. In this way, from the outside of the collecting chamber, the test result displayed on the detection area can be read through the blocking element.

Preferably, when the testing element is mounted on the carrier of the testing element, the blocking element covers and fits to the detection area. Preferably, when the testing element is combined with the collecting chamber, the blocking element attaches to the inner wall of the collecting chamber. In this way, the blocking element occupies the area between the detection area and the inner wall of the collecting chamber. Preferably, the blocking element has a first surface for covering and attaching surface the detection area and a second surface for attaching surface the inner wall of the collecting chamber, and the size of the blocking element is fixed between the first surface and the second surface.

Further, the blocking element is a part of the carrier of the testing element. Further preferably, the carrier of the testing element has a mounting surface, and the mounting surface is provided with a groove for accommodating the testing element, a first connecting surface is the bottom face of the groove, and a second connecting surface is the back of the mounting surface; a distance from the bottom face of the groove to the back surface of the mounting surface is fixed, so that the part of the bottom of the carrier that corresponds to the detection area is transparent.

In a second aspect, the present invention provides a collection and detection device with a detection chamber, the collection and detection device has the advantages of simple structure, low production and assembly cost, and convenient use, and convenience in installation and disassembly of the testing element.

A collection and detection device with a detection chamber comprises a collecting chamber, the collecting chamber has an opening, the detection chamber is located below the opening, and the device is characterized in that the detection chamber is a chamber formed by the side wall of the collecting chamber protruding outward, a side wall of the collecting chamber has two connections to the detection chamber, and a lateral dimension of the detection chamber is greater than or equal to a lateral distance between the two connections. In this way, the testing element is inserted into the detection chamber through the connections between the collecting chamber and the detection chamber and installed in the detection chamber.

Further, the lateral dimension of the detection chamber is fixed; or, the lateral dimension of the detection chamber gradually extends outward from the connections. When the lateral dimension of the detection chamber gradually extends outward from the connections, the lateral dimension of the detections chamber is the smallest at the connection to the collecting chamber.

Further, the detection chamber has a first side wall and a second side wall respectively connected to the two connections, the first side wall and the second side wall are parallel with each other; or, the first side wall and the second side wall are intersected. Preferably, both the first side wall and the second side wall are plane. Preferably, the first side wall and the second side wall are parallel to the axis of the collecting chamber.

Further, the detection chamber has a third side wall for connecting the first side wall and the second side wall, and the third side wall is close to the middle of the collecting chamber relative to an edge of the opening of the collecting chamber. Preferably, the third side wall is a plane. Preferably, the third side wall is parallel to the axis of the collecting chamber.

Further, the detection chamber has a top face, and the top face is connected to the side wall of the collecting chamber and located at an outer edge of the opening of the collecting chamber. Preferably, the top face is a plane. Preferably, the top face is perpendicular to the axis of the collecting chamber.

Further, the detection chamber has a bottom face, and the bottom face is in the same plane as the bottom face of the collecting chamber. Preferably, the bottom face is parallel to the top face.

Further, the detection chamber has a locking structure, and the locking structure comprises a locating element, one end of the locating element that is connected to the bottom of the detection chamber is a connecting end, the other end of the locating element is a free end, and the free end of the locating element is close to the middle of the collecting chamber relative to the connecting end of the locating element. Preferably, the locating element adopts a sheet structure. Preferably, the locating element is close to the third side wall.

Further, the locking structure further comprises a clamping element, and the clamping member is a bulge arranged on the third side wall. The carrier of the testing element has a groove or a straight slot for fitting with the clamping element; when the testing element is installed in the detection chamber, the clamping element is inserted into the groove to achieve installation and fixing of the testing element. Preferably, the clamping element is close to the top of the third side wall. In this way, the locating element fixes a lower side of the testing element; the clamping element fits with the groove of the testing element to achieve fixing of an upper side of the testing element.

Beneficiary effects of the present invention:

1. The structure of the collection and detection device is designed to prevent a fluid in the collecting chamber from entering into an area between the detection area and the inner wall of the collecting chamber, reduce or eliminate the influence of external factors on reading the result in the detection area, thereby making the collection and detection device used more conveniently.

2. The testing element is inserted into and installed in the detection chamber through the opening of the collecting chamber, which reduce the production cost and assembly cost of the collection and detection device.

DETAILED DESCRIPTION

Figure 1:
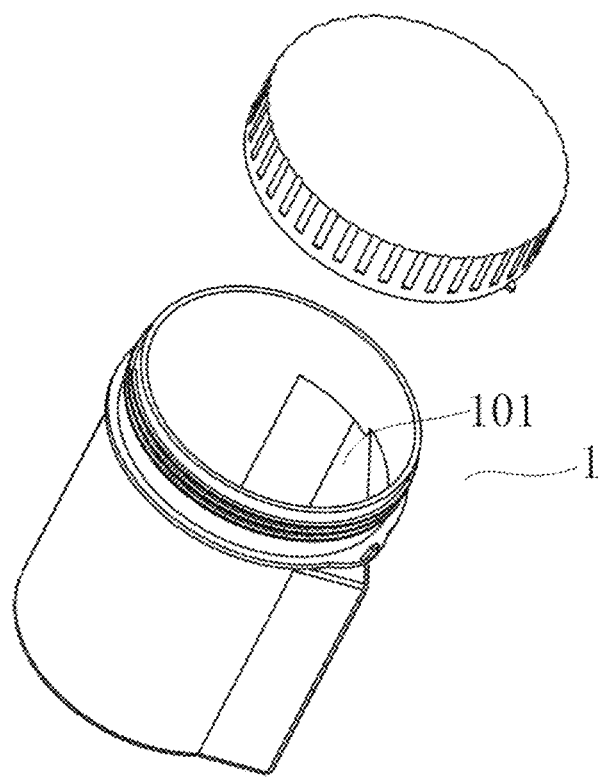
FIG. 1 depicts a stereogram of a collecting chamber according to an embodiment of the present invention.

The following is a further explanation of the structures or of the technical terms involved in the invention, unless specifically specified, they will be understood and interpreted in accordance with the general terms in use in the field.

Detection

Detection means to conduct an experiment or a test to determine a presence of a substance or material. The substance or material, for example, but not limited to chemicals, organic compounds, inorganic compounds, metabolic products, drugs or drug metabolites, organic tissue or metabolites of organic tissues, nucleic acids, proteins, or polymers. In addition, detection can also indicate the quantity of a substance or material tested. Furthermore, a test also means immunity test, chemical test, enzyme test, etc.

Specimen

In the present invention, the specimen collected by the detection device includes a biological fluid. The specimen can be initially liquid, solid or semi-solid. A solid or semi-solid specimen can be converted into a liquid specimen by any suitable method of mixing, crashing, macerating, incubating, dissolving and enzymatic hydrolysis, and then pour into a collecting chamber and be tested for presence of an analyte. The specimen can be taken from a human body, an animal, a plant and nature. The specimen taken from the human body, can be a liquid specimen such as blood, serum, urine, cerebrospinal fluid, sweat, lymph, saliva, gastric fluid; or a solid or semi-solid specimen such as feces, hair, keratin, tartar, nail. The specimen taken from a plant may be solid specimens such as roots, stems and leaves; and also liquid or semi-solid specimens such as tissue fluids and cell fluids prepared from roots, stems and leaves. The specimen taken from the nature can be liquid specimens such as rainwater, river water, seawater, groundwater, etc.; and also solid or semi-solid specimens such as soil, rock, ore, petroleum, etc.

Fluid Exchange

In the present invention, the fluid refers to one or a mixture of gas, air, water vapor, or liquid. Fluid exchange means that a fluid flows from one area to another. Fluid exchange may be a passive exchange of a fluid under the action of an external force or an active exchange for the characteristics of a fluid itself. After a fluid exchange is blocked, the fluid in one area cannot flow to another area. A fluid exchange being blocked does not necessarily mean a presence of a liquid or gas, but, only in some cases, indicates a connection relationship or a state between the two areas; if there is a liquid or a gas in the area, one area is not in fluid communication with the other area.

Testing Element

The testing element refers to a component that can detect an analyte in a sample. The testing element can test an analyte based on any technical principles, for example, immunology, chemistry, electricity, optics, molecular science, physics, etc. The testing element of the present invention may be one kind or a combination of two or more kinds of testing elements. The testing element has a detection area for displaying a detection result, and the detection area displays the detection result after the detection.

A common form of the testing element is a test strip or a lateral flow strip. The test strip may test a test sample based on the principle of immunoassay or chemical analysis, and a non-competitive or competitive analysis mode may be applied. The test strip includes a sample feeding area, a reagent area and a detection area in order. After the test sample is added to the sample feeding area, it flows to the reagent area under a capillary action, reacts with the reagent in the reagent area and then flows further into the detection area under the capillary action, the detection area generates or does not generate a signal, to indicate a presence of an analyte in the test sample. For example, if a T line (Test Line) appears in the detection area, it indicates that there is no analyte in the test sample; if a T line does not appear in the detection area, it indicates that an analyte exists in the test sample. Some test strips also have a control area which is located behind the detection area, a sample flowing through the detection area continues to flow into the control area, and the control area is used for determining whether a test result in the detection area is valid. For example, in some test strips, the test result in the detection area is judged as valid only when a C line (Control Line) appears in the control area, otherwise, the test result in the detection area is invalid. In the present invention, when a test result of the testing element can be read only through the detection area, the detection area of the testing element is the aforesaid detection area; when the test result of the testing element must be judged by a signal generated by a detection area and a control area, the detection area of the testing element includes the detection area and the control area. Of course, in some cases, the test result of the testing element needs to be judged by a signal from other areas, then the detection area also includes the other areas. That is, in the present invention, a complete test result can be read through the detection area of the testing element. Generally, the testing element comprises at least a detection area, through which a presence or absence of an analyte in the sample can be determined. For example, through appearance or change of a color, the general color change is visible through naked eyes, the test result may read through scanning by a scanner, or by taking a picture. Or a fluorescence appears, or a ray appears, etc. Read the test result of the detection area by using a machine or instrument.

The testing element is generally composed of porous absorbent materials, such as any water-absorbing material of filter paper, glass fiber, polyester film, nylon film, paper sheet, non-woven fabric, etc. Generally, the material forming the detection area is of absorbent materials, such as water absorbent film, nitrocellulose film, nylon film, etc.

Analyte

Examples that can use the analyte in the present invention include some hapten substances which include drugs (such as drug of abuse). "Drug of abuse" (DOA) refers to use of drugs for non-medical purposes (usually paralyzing nerves). Abuse of these drugs can lead to physical and mental damage, causing dependence, addiction and/or death. Examples of DOA include cocaine; amphetamine (AMP) (such as black beauty, white amphetamine tablets, dexamphetamine, dextroamphetamine tablets and Beans); methamphetamine (MET) (crank, meth, crystal and speed); barbiturate (BAR) (such as Valium☐, Roche Pharmaceuticals, Nutley and New Jersey); sedatives (i.e. sleeping aids); lysergic acid diethylamide (LSD); inhibitors (downers, goofballs, barbs, blue devils, yellow jackets and methaqualone); tricyclic antidepressants (TCA, i.e. imipramine, amitriptyline and doxepin); methylenedioxy-methamphetamine (MDMA); phencyclidine (PCP); tetrahydrocannabinol (THC, pot, dope, hash, weed, etc.); opiate (i.e. morphine (MOP) or opium, cocaine (COC), heroin and hydroxycodeinone); and antianxietics and sedative hypnotics, wherein antianxietics are a class of drugs mainly used for reducing anxiety, tension and fear, stabilizing mood and having hypnotic and sedative effects, including benzodiazepines (BZO), atypical BZ, fusion diazepines NB23C, benzodiazepines, BZ receptor ligands, ring opening BZ, diphenylmethane derivatives, piperazine carboxylates, piperidine carboxylates, quinazolinones, thiazines and thiazole derivatives, other heterocyclics, imidazole sedatives/paregorics (such as oxycodone (OXY) and methadone (MTD)), propylene glycol derivatives-carbamates, aliphatic compounds, anthracene derivatives, etc. The detection device of the present invention can also be used for detecting drugs that belong to medical use but are prone to overdose, such as tricyclic antidepressants (imipramine or the like) and acetaminophen. After being absorbed by the human body, these drugs will be decomposed into different small molecule substances which are present in body fluids such as blood, urine, saliva, sweat or a part of the body fluid.

For example, the analytes detected by the present invention includes but not limited to, creatinine, bilirubin, nitrite, protein (non-specific), hormone (e.g. human chorionic gonadotropin, progesterone hormone, follicle stimulating hormone, etc.), blood, white blood cell, sugar, heavy metals or toxins, bacterial substance (e.g. proteins or sugars against specific bacteria, such as *Escherichia coli* 0157: H7, staphylococci, salmonella, clostridium, campylobacter, L. monocytogenes, vibrio, or cactus) and substances related to physical characteristics in urine sample, such as pH and specific gravity. Any other clinical chemical analysis of a urine can be detected by combination of a lateral cross-flow detection method and the device of the invention.

Blocking Element
Transparent Area and Detection Area

In the present invention, the position relationship between the transparent area and the detection area reduces the space or distance between the transparent area and the detection area, thereby avoiding exchange with the surrounding fluids such as air, liquid, water vapor, or steam. It can also be understood as it stops, prevent, or reduces the detection area on the testing element from exchanging a liquid or gas with the outside. Furthermore, or, the detection area is in a relatively sealed space, and the sealed space allows the detection area to stay in the sealed space. The case may also be that the detection area and the transparent area are in the sealed space and form a part of the sealed space, and actually the sealed space does not exchange a liquid or gas with the outside, or exchange a mixture of a water vapor and a gas with the outside. For example, the detection area is attached to or covered on a surface of the transparent area so that it can avoid the contact of the air carrying a water vapor with the surface of the transparent area, thus to avoid generation of mists. For example, the detection area and the transparent area form a sealed space or are in a sealed space, the gas, air, water vapor, and liquid outside does not actually enters into the sealed space so that there is no exchange of gas, air, water vapor, or liquid inside and outside the sealed space, thereby the humidity in the sealed space would not be substantially affected; even if a temperature difference exists between the sealed space and the outside, due to low humidity of the sealed space, condensation or reduced possibility of condensation would not occur in the sealed space, thereby avoiding the occurrence of mist, that is to say, the water vapor in the sealed space may condense on the surface of the transparent area. At this time, the detection area is able to or could absorb a liquid sample under the capillary action, and the sample could flow through the detection area under the capillary action. The so-called sealed pace therein does not allow entry of a liquid sample, so as to prevent the liquid, air, and water vapor in other atmospheric environments other than the liquid that is absorbed by the detection area and flows through the detection area under the capillary action from entering into the sealed space. This reduces the formation of mist, liquefaction, or small liquids on the transparent area.

In addition, the contact of the detection area with the transparent area is a partial contact, the case may also be that the entire detection area contacts with the transparent area, or a part of the detection area contacts with a part of the transparent area. Or the distance between the detection area and the transparent area is very close, for example 0-6 mm; if the distance is 0 mm, it indicates the two areas contact with each other; if the distance is more than 0 mm, it indicates a small gap exists between them, such 0.1 mm, 0.2 mm, 0.3 mm, 0.4 mm, 0.5 mm, 0.6 mm, 0.9 mm, 1.0 mm, 1.2 mm, 1.3 mm, 1.5 mm, 2 mm, or 3-5 mm. When the testing element or the detection area is composed of absorbent materials, a liquid flows on the detection area or flows through the detection area under the capillary action. At this time, the sample itself also has a certain temperature, for example, 25-37° C., due to the vapor pressure, the temperature of an ambient air may be lower than the sample temperature; in this case, the liquid on the detection area may evaporate, and the evaporated water vapor would contact the transparent area, and because the temperature of the transparent area is lower than the ambient temperature or the sample temperature, and the water vapor will condense into tiny water droplets and attach to the transparent area. Even if the ambient temperature is lower than the temperature of the liquid flowing through the detection area, the vapor generated in the detection area may condense in the low-temperature transparent area (the vapor pressure of water varies at different temperatures), forming tiny water droplets. Because the absorbent material in the detection area contacts with or adjacent to or close to the transparent area (with a very short distance between), the porous material can absorb the tiny water droplets on the transparent area, thereby reducing the occurrence of mist.

Generally, the material of the transparent area herein is different from that of the detection area, of course, the transparent area may also be formed by the same material as the detection area, such as nylon film or nitrocellulose film. When different materials are used, the detection area uses a porous film, or a porous absorbent material, while the transparent area uses a non-porous material, for example a non-water-absorbent material, such as plastic, metal, PCV, ceramic. The liquid herein is generally a sample that can flow or a sample containing water; the gas herein generally refers to the air in the atmospheric environment, the air may include water vapor and the air may have a certain humidity. When a liquid sample containing water contacts with air, in a micro environment, the liquid sample and air could reach a balanced state, thus generating a corresponding vapor pressure.

Or alternatively, the detection area and the transparent area do not form a sealed space, while the distance between the two is very short, for example 1 mm, 0.5 mm, 0.1 mm, 0.01 mm, 0.05 mm, 1.2 mm, 0 mm (the detection area is attached to the transparent area or stick together or actually close or adjacent to each other), at this time, though there is a small gap between them, it is not considered as a sealed space, but when there is a temperature difference between the transparent and the outside, for example, the temperature of the ambient environment is higher than that of the transparent area, the condensation could occur on the transparent area to form tiny water droplets, which is also called mist phenomenon. However, as the transparent area has a side that directly faces the detection area (front) and a side that does not face the detection area (back), When mist phenomenon is reduced in front of the transparent area, the test result on the actual detection area could be displayed clearer than before.

The material of the transparent area herein is generally transparent, and the detection area on the detection area is read through the transparent area, the transparent material is generally plastic, PVC, transparent film, etc. Of course, these transparent areas may be located on a casing of the detection device, such as a panel, a cup, a test card, or a part of these casings.

Of course, the transparent area may be a multi-layer structure, for example, a combination of multiple transparent layers, as long as they closely contact between the multi-layer transparent areas close to the detection area or there is a small gap, or they are in a sealed chamber, no liquid, air or water vapor could enters into the multi-layer transparent area, thus to reduce the occurrence of mist.

Of course, the mist phenomenon herein refers to mist of sample droplets on the transparent area when flowing over the detection area. Another case is that when the detection area has a distance from the transparent area, the detection area cannot absorb the small droplets by contacting with the transparent area, at this time, there are two embodiments to reduce the mist phenomenon: one is making the detection area and the transparent area in a sealed space to reduce the gas exchange between the space and the outside; the other is treating some chemicals on the surface of the transparent area to reduce mist. For example, some surfactants make the surface of the transparent area more clear, and small droplets are distributed on the surface of the transparent area to increase the clarity of the detection area.

"Misting" is generally a process when there is a temperature difference between two media, for example, there is a temperature difference between the transparent area and the air, for example, the temperature of the transparent area is low, while the temperature of the air is high; and the air generally contains water vapors, when encountering low temperature, water vapors will condense into small droplets. The quantity and speed of droplets produced are directly related to the difference in temperature and the humidity of the air. In a micro environment, if the air humidity is high and the temperature difference is large, the speed of generating small droplets would be fast, and the density on the transparent area would be high; on the contrary, if one of the conditions of the air humidity or temperature difference changes, the quantity and speed of small droplets could be impacted. To reduce the occurrence of mist between the detection area and the transparent area, on one hand, the air humidity should be reduced or the difference between the transparent area and the ambient temperature should be reduced. When using the test device, it is generally hard to quickly change the temperature difference between the transparent area of the detection device and the environment, while the humidity of the air contacting the transparent area can be easily changed, for example, by reducing the amount of humid air from entering into the space between the detection area and the transparent area. Increasing the humidity of the air between the two slowly can reduce the humidity of the air between the two, for example, the humidity of the air between the two increases to the condition where mist occurs in 1 minute, 2 minutes, 10 minutes, 20 minutes, 30 minutes, 50 minutes, 1 hour and 2 hours (with the difference between the transparent area and the ambient temperature unchanged), and when there is a very small gap between the detection area and the transparent area. Or, the humid air is prevented from entering into or actually entering the space between the detection area and the transparent area, for example, a relatively sealed space formed by the detection area and the transparent area. In another embodiment, the detection area contacts with the transparent area or the two have a small gap so that the generated small droplets contacts the detection area, and then absorbed by the detection area composed of porous absorbent materials while forming a liquid, in this way, mist phenomenon in the transparent area is reduced, and the test result is read more clearly.

This is because, in the existing traditional products, the detection area is arranged in an environment wrapped by an outer casing (made of plastic, or PCV material), such as, a pregnancy test device, or on some carriers, or in a test board; for example in the device described in the United States (U.S. Pat. No. 9,414,813, but the detection area of the testing element may have a gas or liquid exchange with the outside. Generally, the area corresponding to the detection area is generally transparent, through which the test result on the detection area can be read (by naked eyes, a scanner, a camera or other equipment) through a transparent part. Generally, the device is pre-stored at a low temperature, and is taken out and incubated for a period of time at the room temperature when a test is required; at this time, as the temperature of the entire detection device is low while the outdoor temperature is high, the water vapor in the outside air will condense into the form of tiny water droplets or mist on the surface of the test device, these tiny water droplets or mist can be wiped off if on the outer surface of the casing, but if they enter into a place between the detection area and the transparent area or enter into an internal space around the detection area, small droplets or mists may form on the transparent inner surface, thus to cover the indication of the test result in the detection area.

In another situation, when the temperature of the external environment is relatively low (such as in winter), and the temperature of the liquid sample is sometimes higher than the temperature of the external environment, for example, the temperature of the urine is 35-37° C., this time, at a low temperature, the temperature of the test device or the temperature of the external casing is generally lower than the temperature of the sample, so there is a temperature difference, at this time, because a gas or liquid exchange with the outside would occur around the detection area, the liquid and the micro atmospheric environment have a moisture exchange, and the humidity in the micro environment increases, then the liquid may also flow into the space around the detection area, or may form tiny water droplets around the detection area or the detection area, thus to form a layer of tiny water droplets on the transparent casing. Sometimes, it may be a combination of the above two factors, in short, the detection device has a temperature difference with the outside and/or the detection device has a temperature difference with the liquid sample, generally when the temperature of the detection device is lower than the outside temperature or/and lower than the temperature of the liquid sample, tiny water droplets will form on the walls around the detection area, this is a process of mist, which forms a pattern like a frosted glass; after detection, a layer of tiny water droplets or something like mists may condense or form on the transparent part, this may affect the accuracy of reading the test result on the detection area. Especially when the detection area is located between positive area or negative area, mist almost covers the result of the detection area, so that the result may not be read or the result may not be read accurately. Sometimes, even if a result is indicated in the detection area, due to the effect of mist, when using a scanner, the result that is consistent with the actual situation cannot be obtained or the test result obtained is wrong.

In some embodiments, the testing element is generally combined with a sample collector or a chamber, for example, the detection device comprises a collecting chamber, and a testing element is installed in the collecting chamber, the testing element has a detection area which is near a side wall of the collecting chamber relative to the back of the detection area, and through the side wall of the collecting chamber the test result displayed in the detection area of the testing element can be read from outside the collecting chamber. However, in the existing detection device, after the testing element is installed in the collecting chamber, there is a gap between the testing element and the inner wall of the collecting chamber, especially a gap between the detection area of the testing element and the inner wall of the collecting chamber, and the gap is in fluid communication with the surroundings (such as other areas or spaces in the collecting chamber), or the gap and the surroundings are in fluid communication state. After the surrounding fluid (such as liquid or air) enters into the gap, mist phenomenon may form in the detection area of the testing element, thereby blocking the detection area of the testing element, at this time, the test result in the detection area cannot be accurately read from outside the collecting chamber, and the use of the detection device may be affected.

The most common example is that when the temperature of the test sample in the collecting chamber is higher than that of the inner wall of the collecting chamber or the environment (for example, when testing a warm body fluid just collected in winter or at a low room temperature), the moisture in the sample evaporates into gas (water vapor), enters into the gap between the detection area of the testing element and the inner wall of the collecting chamber and condenses into water droplets or tiny water droplets or fluid droplets on the inner wall of the collecting chamber. The refraction effect of water droplets on light may cause a deviation between the read test result and the actual test result. For example, because there is a short distance between the detection area and the control area of the test strip, under the refraction effect of water droplets, it may be difficult to judge whether a T line or a C line is indicated. If the water droplets formed are very tiny, the tiny water droplets change the originally smooth and transparent inner wall of the collecting chamber into a form like a "frosted glass", in this case, it is impossible to read the test result cannot from outside the collecting chamber. Another example is that the sample collected in the collecting chamber evaporates into colored gas, and then enters into the gap between the detection area and the inner wall of the collecting chamber, thus to cover the test result. Another example is that when a liquid sample sputters in the collecting chamber, enters into a gap between the detection area of the testing element and the inner wall of the collecting chamber in the form of small droplets and attaches onto the inner wall of the collecting chamber, the test result would be covered, especially when the liquid sample itself is turbid or non-transparent, such as blood, turbid urine, and tissue fluid, the blocking effect may be more obvious.

The present invention designs a collection and detection device which comprises a transparent area and a testing element having a detection area, when the testing element is combined with the transparent area, the transparent area can reduce or block the area between the detection area and the transparent area, and have fluid exchange with the surrounding. In the existing detection device, there is a large gap between the detection area and the inner wall of the collecting chamber, and the detection device is not provided with any component for reducing the size and dimension of the gap, and the gap is in full fluid communication with the surrounding, so that the fluid around the gap can enter into the gap, enables mist, condensation or blocks the test result due to the characteristics of the fluid itself.

The present invention reduces the fluid exchange between the area between the detection area and the transparent area and the surrounding, so that the amount of surrounding fluid entering into the area is reduced, thereby weakening the blocking effect of the fluid on the test result. The reduction of the fluid exchange of the area between the detection area and the transparent area with the surrounding can be any value relative to the existing detection device, for example 5%, 25%, 50%, 80%, 90% . . . , blocking the fluid exchange of the area between the detection area and the inner wall of the transparent area with the surrounding makes no more liquid exchange and gas exchange of the area between the detection area and the inner wall of the transparent area with the surrounding, or no liquid exchange or gas exchange at all. When there is no liquid exchange between the area between the detection area and the inner wall of the transparent area, and the surrounding, after collecting a sample in the collecting chamber, the liquid substance originating from the sample cannot enter into the area between the detection area and the inner wall of the collecting chamber. The liquid substance may be the sample itself, water formed by evaporation and condensation of moisture in the sample, the water solution containing some dissolved substance in the sample, or a substance generated by the sample in other forms. When there is no gas exchange between the area between the detection area and the inner wall of the transparent area, and the surrounding, after collecting a sample in the collecting chamber, the gaseous substance originating from the sample cannot enter into the area between the detection area and the inner wall of the collecting chamber. The gaseous substance may be a substance formed by volatilization, evaporation, reaction of the sample or other forms. When there is no liquid exchange or gas exchange between the area between the detection area and the inner wall of the transparent area, and the surrounding, after collecting a sample in the collecting chamber, the liquid substance and gaseous substance originating from the sample cannot enter into the area between the detection area and the inner wall of the collecting chamber. In some preferred embodiments, a fluid is a gas and/or liquid. In some preferred embodiments, when the testing element is combined with the transparent area, the area between the detection area and the inner wall of the transparent area is gas-sealed. In some preferred embodiments, when the testing element is combined with the transparent area, the area between the detection area and the inner wall of the collecting chamber is liquid-sealed. When no liquid substance enters, if a temperature difference exists, mist is avoided and the result on the detection area can be read correctly.

There are two embodiments to reduce or block the fluid exchange of the area between the detection area and the inner wall of the transparent area, with the surrounding: in the first embodiment, the inner wall of the transparent area attaches to the detection area. For example, the transparent area is a part of a cup collecting chamber, such as a part of the wall of the cup body, a pressure is applied to the back of the testing element to press the detection area of the testing element against the inner wall of the collecting chamber, thereby reducing the size and dimension of the gap between the detection area and the inner wall of the collecting chamber, and even eliminating the gap between the detection area and the inner wall of the collecting chamber. In the second embodiment, the area between the detection area and the inner wall of the transparent area is filled up. That is, the dimension and size of the area between the detection area and the inner wall of the transparent area is reduced by filling the gap. In some preferred embodiments, the area between the detection area and the inner wall of the transparent area can be filled. In some preferred embodiments, the inner wall of the transparent area is made of a transparent or semi-transparent material. In this way, from the outside of the collecting chamber, the test result indicated on the detection area can be read through the transparent area. The blocking element in two embodiments are described in detail below.

In the present invention, the blocking element is a component for reducing or blocking the fluid exchange between the area between the detection area and the inner wall of the collecting chamber and the surrounding. It can also be understood that the blocking element stops, prevents, or reduces the detection area on the testing element from exchanging a liquid or gas with the outside. Furthermore, or, the detection area is in a relatively sealed space, and the sealed space allows the detection area to stay in the sealed space, the case can also be that the detection area and the blocking element are in the sealed space and form a part of the sealed space, and actually the sealed space does not exchange a liquid or gas with the outside, or exchange a mixture of a water vapor and a gas with the outside.

Generally, the material of the blocking element herein is different from that of the detection area, of course, the blocking element may also be formed by the same material as the detection area, such as nylon film or nitrocellulose film. When different materials are used, the detection area uses a porous film, or a porous absorbent material, while the blocking element uses a non-porous material, for example a non-water-absorbent material, such as plastic, metal, PCV, ceramic. The liquid herein is generally a sample that can flow or a sample containing water; the gas herein generally refers to the air in the atmospheric environment, the air may include water vapor and the air may have a certain humidity. When a liquid sample containing water contacts with air, in the a micro environment, a circulation system is formed between the liquid sample and the air for exchange of water vapor.

This is because, in the existing traditional products, the detection area is arranged in an environment wrapped by an outer casing (made of plastic, or PCV material), such as, a pregnancy test device, or on some carriers, or in a test board; for example in the device described in the United States (U.S. Pat. No. 9,414,813, but the detection area of the testing element may have a gas or liquid exchange with the outside. Generally, the area corresponding to the detection area is generally transparent, through which the test result on the detection area can be read (by naked eyes, a scanner, a camera or other equipment) through a transparent part. Generally, the device is pre-stored at a low temperature, and is taken out and incubated for a period of time at the room temperature when a test is required; at this time, as the temperature of the entire detection device is low while the outdoor temperature is high, the water vapor in the outside air will condense into the form of tiny water droplets or mist on the surface of the test device, these tiny water droplets or mist can be wiped off if on the outer surface of the casing, but if they enter into a place between the detection area and the transparent area or enter into an internal space around the detection area, small droplets or mists may form on the transparent inner surface. In another situation, when the temperature of the external environment is relatively low (such as in winter), and the temperature of the liquid sample is sometimes higher than the temperature of the external environment, for example, the temperature of the urine is 35-37° C., this time, at a low temperature, the temperature of the test device or the temperature of the external casing is generally lower than the temperature of the sample, so there is a temperature difference, at this time, because a gas or liquid exchange with the outside would occur around the detection area, the liquid and the micro atmospheric environment have a moisture exchange, and the humidity in the micro environment increases, then the liquid may also flow into the space around the detection area, or may form tiny water droplets around the detection area or the detection area, thus to form a layer of tiny water droplets on the transparent casing. Sometimes, it may be a combination of the above two factors, in short, the detection device has a temperature difference with the outside and/or the detection device has a temperature difference with the liquid sample, generally when the temperature of the detection device is lower than the outside temperature or/and lower than the temperature of the liquid sample, tiny water droplets will form on the walls around the detection area, this is a process of mist, which forms a pattern like a frosted glass; after detection, a layer of tiny water droplets or something like mists may condense or form on the transparent part, this may affect the accuracy of reading the test result on the detection area. Especially when the detection area is located between positive area or negative area, mist almost covers the result of the detection area, so that the result may not be read or the result may not be read accurately. Sometimes, even if a result is indicated in the detection area, due to the effect of mist, when using a scanner, the result that is consistent with the actual situation cannot be obtained or the test result obtained is wrong.

In some embodiments, the testing element is generally combined with a sample collector or a chamber, for example, the detection device comprises a collecting chamber, and a testing element is installed in the collecting chamber, the testing element has a detection area which is near a side wall of the collecting chamber relative to the back of the detection area, and through the side wall of the collecting chamber the test result displayed in the detection area of the testing element can be read from outside the collecting chamber. However, in the existing detection device, after the testing element is installed in the collecting chamber, there is a gap between the testing element and the inner wall of the collecting chamber, especially a gap between the detection area of the testing element and the inner wall of the collecting chamber, and the gap is in fluid communication with the surroundings (such as other areas or spaces in the collecting chamber), or the gap and the surroundings are in fluid communication state. After the surrounding fluid (such as liquid or air) enters into the gap, mist phenomenon may form in the detection area of the testing element, thereby blocking the detection area of the testing element, at this time, the test result in the detection area cannot be accurately read from outside the collecting chamber, and the use of the detection device may be affected. The most common example is that when the temperature of the test sample in the collecting chamber is higher than that of the inner wall of the collecting chamber or the environment (for example, when testing a warm body fluid just collected in winter or at a low room temperature), the moisture in the sample evaporates into gas, enters into the gap between the detection area of the testing element and the inner wall of the collecting chamber and condenses into water droplets or tiny water droplets or fluid droplets on the inner wall of the collecting chamber. The refraction effect of water droplets on light may cause a deviation between the read test result and the actual test result. For example, because there is a short distance between the detection area and the control area of the test strip, under the refraction effect of water droplets, it may be difficult to judge whether a T line or a C line is indicated. If the water droplets formed are very tiny, the tiny water droplets change the originally smooth and transparent inner wall of the collecting chamber into a form like a "frosted glass", in this case, it is impossible to read the test result cannot from outside the collecting chamber. Another example is that the sample collected in the collecting chamber evaporates into colored gas, and then enters into the gap between the detection area and the inner wall of the collecting chamber, thus to cover the test result. Another example is that when a liquid sample sputters in the collecting chamber, enters into a gap between the detection area of the testing element and the inner wall of the collecting chamber in the form of small droplets and attaches onto the inner wall of the collecting chamber, the test result would be covered, especially when the liquid sample itself is turbid or non-transparent, such as blood, turbid urine, and tissue fluid, the blocking effect may be more obvious.

The present invention designs a collection and detection device which comprises a blocking element, when the testing element is combined with a collecting chamber, the blocking element reduces or blocks the fluid exchange between the area between the detection area and an inner wall of the collecting chamber and the surrounding. In the existing detection device, there is a gap between the detection area and the inner wall of the collecting chamber, and the detection device is not provided with any component for reducing the size and dimension of the gap, and the gap is in full fluid communication with the surrounding, so that the fluid around the gap can enter into the gap, enables mist, condensation or blocks the test result due to the characteristics of the fluid itself. The present invention reduces the fluid exchange between the area between the detection area and the inner wall of the collecting chamber and the surrounding through a blocking element, so that the amount of surrounding fluid entering into the area is reduced, thereby weakening the blocking effect of the fluid on the test result. The reduction of the fluid exchange of the area between the detection area and the inner wall of the collecting chamber with the surrounding can be any value relative to the existing detection device, for example 5%, 25%, 50%, 80%, 90% . . . , blocking the fluid exchange of the area between the detection area and the inner wall of the collecting chamber with the surrounding makes no more liquid exchange and gas exchange of the area between the detection area and the inner wall of the transparent area with the surrounding, or no liquid exchange or gas exchange at all. When there is no liquid exchange between the area between the detection area and the inner wall of the collecting chamber and the surrounding, after collecting a sample in the collecting chamber, the liquid substance originating from the sample cannot enter into the area between the detection area and the inner wall of the collecting chamber. The liquid substance may be the sample itself, water formed by evaporation and condensation of moisture in the sample, the water solution containing some dissolved substance in the sample, or a substance generated by the sample in other forms. When there is no gas exchange between the area between the detection area and the inner wall of the collecting chamber, and the surrounding, after collecting a sample in the collecting chamber, the gaseous substance originating from the sample cannot enter into the area between the detection area and the inner wall of the collecting chamber. The gaseous substance may be a substance formed by volatilization, evaporation, reaction of the sample or other forms. When there is no liquid exchange or gas exchange between the area between the detection area and the inner wall of the collecting chamber, and the surrounding, after collecting a sample in the collecting chamber, the liquid substance and gaseous substance originating from the sample cannot enter into the area between the detection area and the inner wall of the collecting chamber. In some preferred embodiments, a fluid is a gas and/or liquid. In some preferred embodiments, when the testing element is combined with the collecting chamber, the area between the detection area and the inner wall of the collecting chamber is gas-sealed. In some preferred embodiments, when the testing element is combined with the collecting chamber, the area between the detection area and the inner wall of the collecting chamber is liquid-sealed. When no liquid substance enters, if a temperature difference exists, mist is avoided and the result on the detection area can be read correctly.

In the present invention, the blocking element only reduces or blocks the fluid exchange between the area between the detection area and an inner wall of the collecting chamber and the surrounding during the detection process, for example, the detection process starts with collection of a sample in the collecting chamber and ends with reading a test result. Of course, the blocking element acts on its effect of reducing or blocking the fluid exchange before collecting a sample in the collecting chamber and continues the effect until a test result is read; or, from time of combination of the testing element and the collecting chamber, the blocking element continues to exert the effect of reducing or blocking the fluid exchange. As along as the blocking element reduces or blocks the fluid exchange between the area between the detection area and an inner wall of the collecting chamber and the surrounding, the interference of external factors on reading a test result is reduced or avoided.

There are two embodiments to reduce or block the fluid exchange between the area between the detection area and the inner wall of the collecting chamber and the surrounding: in the first embodiment, the blocking element makes the detection area attached to the inner wall of the collecting chamber. In other words, the blocking element applies a pressure to the back of the testing element and presses the detection area of the testing element against the inner wall of the collecting chamber, thereby reducing the size and dimension of the gap between the detection area and the inner wall of the collecting chamber, and even eliminating the gap between the detection area and the inner wall of the collecting chamber. In the second embodiment, the blocking element fills up the area between the detection area and the inner wall of the collecting chamber; That is, the dimension and size of the area between the detection area and the inner wall of the collecting chamber is reduced by filling the gap. In some preferred embodiments, the blocking element fills up the area between the detection area and the inner wall of the transparent area. In some preferred embodiments, the blocking element is made of a transparent or semi-transparent material. In this way, from the outside of the collecting chamber, the test result displayed on the detection area can be read through a second blocking element. The blocking element in two embodiments are described in detail below.

In the first embodiment: the blocking element makes the detection area attached to the inner wall of the collecting chamber.

When the testing element is combined with the collecting chamber, the detection area is clamped between the detection area and the inner wall of the collecting chamber. In some preferred embodiments, the blocking element comprises a clamping area for fitting the inner wall of the collecting chamber and clamping the detection area; when the testing element is combined with the collecting chamber, the detection area is clamped between the clamping area and the inner wall of the collecting chamber. For example, the blocking element may be a carrier of the testing element, and the carrier of the testing element has a groove for accommodating the testing element, and the clamping area is a bottom face of the groove; or, the clamping area is a bump arranged in the groove.

In some preferred embodiments, when the testing element is combined with the collecting chamber, the clamping area covers the back of the detection area and the clamping area attaches to the back of the detection area. The testing element has a certain thickness, the back of the detection area refers to the side of the testing element that faces away from the detection area, and the back of the detection area have the same shape, dimension and size as the detection area. In this way, the clamping area can apply a pressure to the entire detection area through the back of the detection area, and press the entire detection area against the inner wall of the collecting chamber, thereby attaching the inner wall of the collecting chamber to the detection area.

There may one, two or more testing elements; and correspondingly, there may be one, two or more detection areas. In some preferred embodiments, there is one clamping area, and the clamping area covers all the back of the detection areas; or, there are two or more clamping areas, and each clamping area covers one, two or more back of the detection areas. When there are two or more clamping areas, the quantity of detection areas covered by the two or more clamping areas may be the same or different. For example, each clamping area covers the back of one detection area; or, each clamping area covers the back of two detection areas; or, each clamping area covers the back of three detection areas . . . or, a first clamping area covers the back of one detection area, a second clamping area covers the back of two detection areas, and a third clamping area covers the back of three detection areas . . . .

In some preferred embodiments, the inner wall of the collecting chamber has a attaching area for attaching surface the detection area and the attaching area covers the detection area; when the testing element is combined with the collecting chamber, the detection area is clamped between the clamping area and the attaching area. The entire detection area attaches to the attaching area so that a complete test result in the detection area can be accurately read from outside the collecting chamber, In some preferred embodiments, the attaching area is a partial area of the inner wall of the collecting chamber; or, the attaching area is a bulge arranged on the inner wall of the collecting chamber.

There may one, two or more testing elements; and correspondingly, there may be one, two or more detection areas. In some preferred embodiments, there is one attaching area, and the attaching area covers all the detection areas; or, there are two or more attaching areas, and each attaching area covers one, two, or more detection areas. When there are two or more attaching areas, the quantity of detection areas covered by the two or more attaching areas may be the same or different. For example, each attaching area covers one detection area; or, each attaching area covers two detection areas; or, each attaching area covers three detection areas . . . or, a first attaching area covers one detection area, a second attaching area covers two detection areas, and a third attaching area covers three detection areas . . . .

The detection area of the testing element has a fixed thickness, After the detection area is clamped between the attaching area and the clamping area, the thickness of the detection area should also be uniform, so that the test sample passes through the detection area at a constant speed, thus to make the test more accurate. Hence, when the testing element is installed in a collecting chamber, the clamping area needs to apply an equal pressure to each part of the detection area. In some preferred embodiments, the clamping area has a clamping surface for contacting the back of the detection area, and the attaching area has a attaching surface for contacting the detection area; when the testing element is combined with the collecting chamber, the clamping surface is parallel to the attaching surface. In this way, when the testing element is installed in the collecting chamber, the distance between the attaching surface and the clamping surface is a fixed value, so that the clamping area can apply an equal pressure to each part of the detection area. In some embodiments, the attaching surface and the clamping surface are plane surfaces, curved surfaces, or arc surfaces.

In order to make the detection area firmly clamped between the attaching area and the clamping area, in some preferred embodiments, when the testing element is combined with the collecting chamber, the distance between the attaching surface and the clamping surface is less than or equal to the thickness of the detection area. Thickness of the detection area means the thickness of the area where the detection area of the testing element is located. When the distance between the attaching surface and the clamping surface is less than the thickness of the detection area, after the detection area clamped between the attaching area and the clamping area is applied with a certain pressure, the detection area firmly attaches to the attaching surface of the attaching area. When the distance between the attaching surface and the clamping surface is equal to the thickness of the detection area, though the detection area clamped between the attaching area and the clamping area is not subject to a pressure of the attaching area and the clamping area, the detection area still could attach to the attaching surface of the attaching area. Additionally, the detection area can display the test result only when the test sample flows through the detection area. After the testing element is installed in the collecting chamber, if the distance between the attaching area and the clamping area is less than zero, the attaching area will hinder the installation of the testing element; if the distance between the attaching area and the clamping area is zero, then the thickness of the detection area is close to zero when the detection area is clamped by the attaching area and the clamping area, thereby blocking the flow of the test sample in the detection area and affecting the detection process. Therefore, in some preferred embodiments, when the testing element is combined with the collecting chamber, the distance between the attaching surface and the clamping surface is greater than zero.

When fitting of attaching area and the clamping area, and clamping of the detection area may can be achieved according to the following embodiments, for example, the carrier of the testing element being used as a blocking element. The carrier of the testing element is a component for fixing the testing element, and the testing element can be installed into the collecting chamber through the carrier of the testing element. When the testing element is installed in the collecting chamber through the carrier of the testing element, the combination of the testing element and the collecting chamber depends on the combination of the carrier of the testing element and the collecting chamber. The detection device comprises a collecting chamber, a testing element, and a carrier of the testing element, wherein the testing element has a detection area, When the testing element is combined with the collecting chamber, the detection area is sandwiched between the testing element carrier and the inner wall of the collecting chamber, and the detection area and the inner wall of the collecting chamber fit.

The first embodiment: the testing element carrier has a groove for accommodating the testing element. When the testing element is combined with the collecting chamber, the distance between the bottom face of the groove and the inner wall of the collecting chamber is less than or equal to the thickness of the detection area. In this way, when the testing element and the collecting chamber are combined, the detection area is clamped between the bottom face of the groove and the inner wall of the collecting chamber, and the detection area is attached to the inner wall of the collecting chamber. That is to say, the clamping area is a bottom face of the groove, and the attaching area is a partial area of the inner wall of the collecting chamber corresponding to the clamping area. In some embodiments, the bottom face of the groove is parallel to the inner wall of the collecting chamber. The inner wall of the collecting chamber may be a plane surface, a curved surface, a cylindrical surface or a conical cylindrical surface. The second embodiment: the carrier of the testing element has a groove for accommodating the testing element, and a bump is arranged in the groove, when the testing element is combined with the collecting chamber, the detection area is clamped between the bump and the inner wall of the collecting chamber, and the detection area is attached to the inner wall of the collecting chamber. That is to say, the clamping area is a bump arranged in the groove on the carrier of the testing element; the area of the inner wall of the collecting chamber corresponding to the bump is considered as an attaching area, or as an attaching surface of the attaching area. When installing the testing element, first install the testing element in the groove on the carrier of the testing element, and then install the carrier of the testing element together with the testing element in the collecting chamber; when the carrier of the testing element is properly installed, the bump in the groove on the carrier of the testing element fits with the inner wall of the collecting chamber, thus to clamp the detection area of the testing element.

In some preferred embodiments, one end of the bump is connected to the groove, and the other end of the bump is a free end; when the testing element is combined with a collecting chamber, the free end face of the bump covers the back of the detection area, and the free end of the bump attaches to the back of the detection area. The free end face of the bump is a face at the free end of the bump, that is, the clamping surface of the clamping area. In this way, when the testing element is combined with the collecting chamber, the bump applies a pressure to the back of the detection area and presses the entire detection area against an inner wall of the collecting chamber, so that the inner wall of the collecting chamber fully covers and attaches to the detection area.

The carrier of the testing element has a mounting surface, and the groove is a groove recessed from the mounting surface. The free end face of the bump may locate outside the groove, flush with the groove, or arranged in the groove. That is to say, the height of the bump may be greater than, equal to or less than the depth of the groove. The free end face of the bump is flush with the groove, that is, the free end face of the bump is in the same plane as the mounting surface. A bump is arranged in the groove, and the bump makes the detection area of the testing element protrude out of the groove relative to other areas of the testing element. However, if the detection area is completely outside the groove, then the two side walls of the groove cannot constrain the detection area, and the testing element can easily withdraw from the groove. In some preferred embodiments, the free end face of the bump is located inside the groove. That is to say, the height of the bump is less than the depth of the groove, and the entire bump is located inside the groove. In this way, the detection area of the testing element can be wholly or partially constrained by the two side walls of the groove, so as to increase the installation stability of the testing element in the groove and makes it difficult for the testing element to withdraw from the groove. The distance from the free end face of the bump to the mounting surface may be less than or equal to the thickness of the detection area. When the distance from the free end face of the bump to the mounting surface is less than the thickness of the detection area, a part of the detection area can be constrained by the two side walls of the groove; when the distance from the free end face of the bump to the mounting surface is equal to the thickness of the detection area, the detection area can be completely constrained by both side walls of the groove. If the distance from the free end face of the bump to the mounting surface is greater than the thickness of the detection area, then when the testing element is installed in the collecting chamber, with interference of the mounting surface, the inner wall of the collecting chamber could not contact the detection area, and even could not fit with the bump to clamp the detection area.

There may be one, two or more testing elements; and correspondingly, the carrier of the testing element may have one, two or more grooves for installing the testing element. When the free end face of the bump is located inside the groove, in some preferred embodiments, when there are two or more grooves, each groove has its own bump. When the testing element is installed in the collecting chamber, the distance between the free end face of two or more bumps and the inner wall of the collecting chamber may be the same or different. In order to facilitate the installation of the testing element and the manufacture of the carrier of the testing element, generally when there are more than two testing elements, the more than two testing elements or the detection area of more than two testing elements have the same thickness. Therefore, in some preferred embodiments, the distance between the free end face of the two or more bumps and the inner wall of the collecting chamber is equal. When the free end face of the bump is outside the groove or flush with the groove, in some other embodiments, when two or more grooves are arranged, there may be only one bump, and the bump penetrates through all the grooves and covers the back of all the detection areas; or, there are two or more bumps, and the bumps penetrate through two or more grooves cover the back of the two or more detection areas. When there are two or more bumps, the quantity of back sides of the detection area covered by each bump may be the same or different.

In some preferred embodiments, when the testing element is installed in a collecting chamber, a free end face of the bump must be parallel to an inner wall of the collecting chamber. In some preferred embodiments, the inner wall of the collecting chamber may be a plane surface, a curved surface, a cylindrical surface or a conical cylindrical surface. In some preferred embodiments, when the testing element is installed in a collecting chamber, the distance from a free end face of the bump to an inner wall of the collecting chamber is less than or equal to the thickness of the detection area. In some preferred embodiments, when the testing element is installed in a collecting chamber, the distance from a free end face of the bump to an inner wall of the collecting chamber is greater than zero.

The third embodiments: the carrier of the testing element has a groove for accommodating the testing element, and a bulge is arranged in the groove, when the testing element is installed in the collecting chamber, the detection area is clamped between the bulge and the groove, and the detection area is attached to the bulge. That is to say, the attaching area is a bulge arranged in an inner wall of the collecting chamber; a bottom face of the groove corresponds to the bulge, or the area corresponding to the bulge is considered as a clamping area, or a clamping surface. When installing the testing element, first install the testing element in the groove on the carrier of the testing element, and then install the carrier of the testing element together with the testing element in the collecting chamber; when the carrier of the testing element is properly installed, the bump on the inner wall of the collecting chamber is pressed against the detection area of the testing element in the groove, so that the bump fits with the bottom face of the groove, thus to clamp the detection area of the testing element.

In some preferred embodiments, one end of the bulge is a connecting end connected to an inner wall of a collecting chamber, and the other end of the bulge is a free end; when the testing element is installed in the collecting chamber, the free end face of the bulge covers the detection area, and the free end face of the bump attaches to the detection area. The free end face of the bulge is also an attaching surface. In some preferred embodiments, the connecting end of the bulge covers the detection area. In some preferred embodiments, the size of the bulge is fixed, for example, the bulge is a cuboid, a cube or a cylinder; or the size of the bulge increases from the free end to the connecting end of the bulge, for example, the bulge is a triangular pyramid, a rectangular pyramid, or a conical-cylinder.

In some preferred embodiments, when the testing element is installed in the collecting chamber, the bulge is inserted in the groove or the bulge is placed outside the groove. The testing element has a certain thickness, the thickness of the testing element may be greater than, less than, or equal to the depth of the groove on the carrier of the testing element. If the thickness of the detection area of the testing element is greater than the depth of the groove, when the testing element is installed in the groove on the carrier of the testing element, a part of the detection area of the testing element is exposed out of the groove; if the thickness of the detection area of the testing element is equal to or less than the depth of the groove, when the testing element is installed in the groove on the carrier of the testing element, the detection area of the testing element is completely located in the groove. When the thickness of the detection area of the testing element is greater than or equal to the depth of the groove, the position relationship between the bulge and the groove has two options: first, the distance between the free end face of the bulge and the bottom face of the groove is equal to the thickness of the detection area, and the bulge is located outside the groove; second, the distance between the free end face of the bulge and the bottom face of the groove is less than the thickness of the detection area, the bulge may be located outside the groove, or partially inserted into the groove. When the thickness of the detection area of the testing element is less than the depth of the groove, to ensure the bulge fits with the groove and clamps the detection area and make the free end face of the bulge cover and attach to the detection area, the bulge must be inserted in the groove.

There may be one, two or more testing elements; and correspondingly, the carrier of the testing element may have one, two or more grooves for installing the testing element. In some preferred embodiments, there may be one bulge, and the free end face of the bump covers and attaches to all the detection areas; or there may be two or more bulges, the free end face of each bulge covers one, two or more detection areas. For example, if when the bulge is outside the groove, the bulge can fit with the bottom face of the groove and clamps the detection area and the free end face of the bulge can be attached to the detection area; there may be one bulge, and the free end face of the bump covers and attaches to all the detection areas; or there may be two or more bulges, the free end face of each bulge covers one, two or more detection areas. If when the bulge is inserted the groove, the bulge can fit with the bottom face of the groove and clamps the detection area and the free end face of the bulge can be attached to the detection area; the groove, the detection area and the bulge correspond to each other, so when there are two or more grooves, accordingly, there should be two or more bulges.

In some preferred embodiments, when the testing element is installed in the collecting chamber, the free end face of the bulge is parallel to the bottom face of the groove. In this way, the distance between the free end face of the bulge and the bottom face of the groove is fixed. In some preferred embodiments, the free end face of the bulge is a plane surface, a curved surface, a cylindrical surface or a conical cylindrical surface. In some preferred embodiments, when the testing element is installed in a collecting chamber, the distance from a free end face of the bulge to a bottom face of the groove is less than or equal to the thickness of the detection area. In some preferred embodiments, when the testing element is installed in a collecting chamber, the distance from a free end face of the bulge to a bottom face of the groove is greater than zero.

The fourth embodiment: the carrier of the testing element has a groove for accommodating the testing element, and a bump is arranged in the groove, when the testing element is installed in the collecting chamber, the bulge corresponds to the bump, the detection area is clamped between the bulge and the bump, and the detection area is attached to the bulge. In this embodiment, the clamping area is a bump arranged in the groove, and the attaching area is a bulge arranged in an inner wall of the collecting chamber;

In some preferred embodiments, one end of the bulge is connected to an inner wall of a collecting chamber, and the other end of the bulge is a free end; when the testing element is installed in the collecting chamber, the free end face of the bulge covers the detection area, and the free end face of the bump attaches to the detection area. The free end face of the bulge is an attaching surface.

In some preferred embodiments, one end of the bump is connected to the groove, and the other end of the bump is a free end; when the testing element is installed in a collecting chamber, the free end face of the bump covers the back of the detection area, and the free end of the bump attaches to the back of the detection area. The free end face of the bump is a clamping surface.

In some preferred embodiments, when the testing element is installed in a collecting chamber, the free end face of the bump covers is parallel to the free end face of the bulge. In this way, the distance between the free end face of the bulge and the free end face of the bulge is fixed. The free end face of the bulge is a plane surface, a curved surface, a cylindrical surface or a conical cylindrical surface.

To ensure the testing element is firmly installed in the groove on the carrier of the testing element, without easily withdrawing out of the groove, in some preferred embodiments, the free end face of the bump is locate inside the groove; when the testing element is combined with the collecting chamber, the bulge is inserted in the groove or the bulge is placed outside the groove. When the testing element is installed in a groove on the carrier of the testing element, the thickness of the detection area is greater than, equal to or less than the distance from a free end face of the bump to the mounting surface. When the thickness of the detection area is greater than the distance from a free end face of the bump to the mounting surface, a part of the detection area is exposed out of the groove; the thickness of the detection area is less than or equal to the distance from a free end face of the bump to the mounting surface. The detection area is completely contained in the groove. When the thickness of the detection area is greater than or equal to the distance between the free end face of the bump and the mounting surface, the position relationship between the bulge and the groove has two options: first, the distance between the free end face of the bulge and the free end face of the bump is equal to the thickness of the detection area, and the bulge is located outside the groove; second, the distance between the free end face of the bulge and the free end face of the bump is less than the thickness of the detection area, the bulge may be located outside the groove, or partially inserted into the groove. When the thickness of the detection area is less than the distance from the free end face of the bump to the mounting surface, the bulge must be inserted in the groove so that it can fit with the bump, thus to achieve the clamping, covering and attaching of the detection area.

In some preferred embodiments, each groove has its own bump. In some preferred embodiments, there may be one bulge, and the free end face of the bump covers and attaches to all the detection areas; or there may be two or more bulges, the free end face of each bulge covers one, two or more detection areas.

In some preferred embodiments, when the testing element is installed in a collecting chamber, the distance from a free end face of the bulge to a free end face of the bump is less than or equal to the thickness of the detection area. In some preferred embodiments, when the testing element is installed in a collecting chamber, the distance from a free end face of the bulge to a free end face of the bump is zero. In this way, it can avoid mutual interference between the bulge and the bump when the testing element is installed in the collecting chamber, which may hinder the installation of the testing element (when the distance between the free end face of the bulge and the free end face of the bump is less than zero), and can also avoid blocking the flow of the test sample in the detection area due to excessive force formed by the bulge and the bump on the detection area (when the distance between the free end face of the bulge and the free end face of the bump is equal to zero).

The blocking element fills up the area between the detection area and the inner wall of the collecting chamber.

The blocking element reduces or eliminate the gap between the detection area and the inner wall of the collecting chamber by filling up the area between the detection area and the inner wall of the collecting chamber, thereby reducing or blocking the fluid exchange between the area between the detection area and the inner wall of the collecting chamber and the surrounding. In this way, when the testing element is combined with the collecting chamber, the blocking element is located between the detection area and the inner wall of the collecting chamber, and the detection area is close to the carrier of the testing element relative to the back of the detection area. In some preferred embodiments, the blocking element is made of a transparent or semi-transparent material. The transparent or semi-transparent materials, for example, may be plastic, glass, gels, etc.

The blocking element may be fixedly connected or detachably connected to the inner wall of the collecting chamber. For example, the blocking element is a transparent adhesive sheet which is covered on the whole detection area, and the whole detection area is stuck to the inner wall of the collecting chamber through the adhesive sheet, thereby connecting the blocking element firmly to the detection area and the and the inner wall of the collecting chamber. However, the adhesive sheet contains a volatile substance, which may affect the detection accuracy of the testing element. Moreover, since the testing element is generally disposable, after the detection area is fixedly connected to the inner wall of the collecting chamber, the collecting chamber may not use it any more. Therefore, the preferred embodiment is that the blocking element is detachably connected to the inner wall of the collecting chamber. In some preferred embodiments, the blocking element is detachably connected to the inner wall of the collecting chamber. In some embodiments, the blocking element is fixedly connected or detachably connected to the detection area.

In order to enable the blocking element to reduce the gap between the detection area and the inner wall of the collecting chamber as possible, in some preferred embodiments, the blocking element can fill up the area between the detection area and the inner wall of the collecting chamber. In some preferred embodiments, when the testing element is installed on the carrier of the testing element, the blocking element covers and attaches to the detection area. In some preferred embodiments, when the testing element is combined with the collecting chamber, the blocking member is attached to the inner wall of the collecting chamber. In some preferred embodiments, the blocking element has a first connecting surface for covering and attaching to the detection area and a second connecting surface for attaching to the inner wall of the collecting chamber, the size of the blocking element is fixed from the first connecting surface to the second connecting surface; or the size of the blocking element gradually increases from the first connecting surface to the second connecting surface.

In some embodiments, a connecting area is arranged in the inner wall of the collecting chamber for attaching to the blocking element, and the connecting area is a bulge on the inner wall of the collecting chamber.

In some preferred embodiments, the blocking element may be a carrier of the testing element. The carrier of the testing element has a mounting surface, and the mounting surface has a groove for accommodating the testing element; after the carrier of the testing element is installed in the groove, the detection area is attached to the bottom face of the groove, when the testing element is combined with the collecting chamber, the back of the mounting surface of the testing element carrier is attached to the inner wall of the collecting chamber, so that the carrier of the testing element fills out the area between the detection area and the inner wall of the collecting chamber. At this time, the bottom face of the groove is the first connecting surface of the blocking element, and the back face of the mounting surface of the testing element carrier is the second connecting surface.

In some preferred embodiments, the blocking element is fixedly or detachably connected to the detection area. For example, when the testing element is installed on the groove in the carrier of the testing element, the testing element can be fixedly connected to the groove, or the testing element and the groove can be detachably connected through a clamping structure in the groove.

Collecting Chamber

The collecting chamber is a chamber for containing a sample. In order to activate the detection function of the collection and detection device, the testing element is installed in the collecting chamber before sample collection. In order to facilitate the installation of the testing element, the existing collection and detection device designs a collecting chamber which comprises two or more components, and the testing element is installed and dismantled by disassembly and assembly of the two or more components, which has the disadvantages of inconvenient operation, and high processing and assembly cost. Therefore, the present inventions designs a collection and detection device with a detection chamber, comprising a collecting chamber, the collecting chamber has an opening, the detection chamber is located below the opening, and the device is characterized in that the detection chamber is a chamber formed by the inner wall of the collecting chamber protruding outward, a side wall of the collecting chamber has two connections to the detection chamber, and a lateral dimension of the detection chamber is greater than or equal to a lateral distance between the two connections. Assume that the collecting chamber is cut by a transverse section, and the transverse section respectively intersects with the two connections between the side wall of the collecting chamber and the detection chamber to form a first connection point and a second connection point, the lateral distance between the two connections refers to the distance between the first connection point and the second connection point. Assume that the collecting chamber is cut by a longitudinal section, and the longitudinal section is perpendicular to the transverse section and also parallel to a connecting line between the two connection points, the longitudinal section, the transverse section and the side wall of the detection chamber intersect with each other to form two intersection points; the lateral dimension of the detection chamber refers to the distance between two intersections. Lateral direction refers to the direction perpendicular to the axis of the collecting chamber. Longitudinal direction refers to the direction parallel to the axis of the collecting chamber. In this way, the testing element is inserted into the detection chamber through the connection between the collecting chamber and the detection chamber, and is installed in the detection chamber so that it is convenient to operate; and the collecting chamber is integrally formed, and the processing cost is low.

In some preferred embodiments, the lateral dimension of the detection chamber is fixed; or, the lateral dimension of the detection chamber gradually extends outward from the connections. When the lateral dimension of the detection chamber gradually extends outward from the connections, the lateral dimension of the detections chamber is the smallest at the connection to the collecting chamber.

In some preferred embodiments, the detection chamber has a first inner wall and a second inner wall respectively connected to the two connections, the first inner wall and the second inner wall are parallel with each other; or, the first inner wall and the second inner wall are intersected. In some preferred embodiments, both the first side wall and the second side wall are plane. In some preferred embodiments, the first side wall and the second side wall are parallel to the axis of the collecting chamber.

In some preferred embodiments, the detection chamber has a third side wall for connecting the first side wall and the second side wall, and the third side wall is close to the middle of the collecting chamber relative to an edge of the opening of the collecting chamber. In some preferred embodiments, the third side wall is a plane. In some preferred embodiments, the third side wall is parallel to the axis of the collecting chamber.

In some preferred embodiments, the detection chamber has a top face, and the top face is connected to the side wall of the collecting chamber and located at an outer edge of the opening of the collecting chamber. In some preferred embodiments, the top face is a plane. In some preferred embodiments, the top face is perpendicular to the axis of the collecting chamber.

In some preferred embodiments, the detection chamber has a bottom face, and the bottom face is in the same plane as the bottom face of the collecting chamber. In some preferred embodiments, the bottom face is parallel to the top face.

In some preferred embodiments, the detection chamber has a locking structure, and the locking structure comprises a locating element, one end of the locating element that is connected to the bottom of the detection chamber is a connecting end, the other end of the locating element is a free end, and the free end of the locating element is close to the middle of the collecting chamber relative to the connecting end of the locating element. In some preferred embodiments, the locating element is close to the third side wall.

In some preferred embodiments, the locking structure further comprises a clamping element, and the clamping member is a bulge arranged on the third side wall. The testing element has a groove or a straight slot for fitting with the clamping element; when the testing element is installed in the detection chamber, the clamping element is inserted into the groove to achieve installation and fixing of the testing element. In some preferred embodiments, the clamping element is close to the top of the third side wall. In this way, the locating element fixes a lower side of the testing element; the clamping element fits with the groove of the testing element to achieve fixing of an upper side of the testing element.

DETAILED DESCRIPTION OF EMBODIMENTS

Combining the detailed description of embodiments, the present invention is further described as follows.

A collection and detection device comprises a collection chamber and a testing element, wherein the testing element has a detection area; the device is characterized in that the collection and detection device comprises a blocking element, when the testing element is combined with the collecting chamber, the blocking element reduces or blocks the fluid exchange between the area between the detection area and an inner wall of the collecting chamber and the surrounding.

In some embodiments, a fluid is a gas and/or liquid. In some embodiments, when the testing element is combined with the collecting chamber, the area between the detection area and the inner wall of the collecting chamber is gas-sealed. In some embodiments, when the testing element is combined with the collecting chamber, the area between the detection area and the inner wall of the collecting chamber is liquid-sealed.

The blocking element reduces or blocks the fluid exchange between the area between the detection area and an inner wall of the collecting chamber and the surrounding by attaching the detection area to the inner wall of the collecting chamber, for example as described in the embodiments 1-3; or the blocking element reduces or eliminate the gap between the detection area and the inner wall of the collecting chamber by filling up the area between the detection area and the inner wall of the collecting chamber, for example as described in the embodiment 4. The attaching therein is a firmly connected state.

Combining the drawings, the invention is further described as follows, the descriptions only illustrates the realization of the preferred embodiments, and do not constitute any limitation to the present invention.

Embodiment 1

Figure 3:
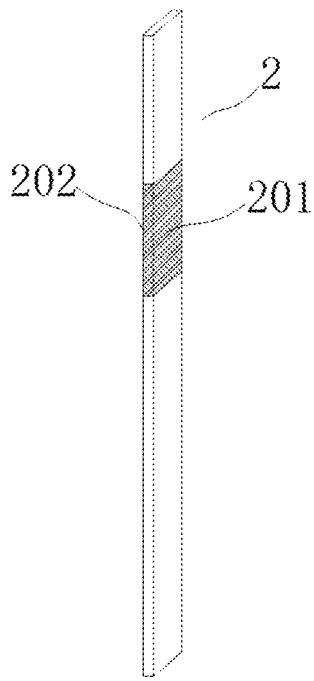
FIG. 3 depicts a schematic diagram of a testing element according to an embodiment of the present invention.
Figure 4:
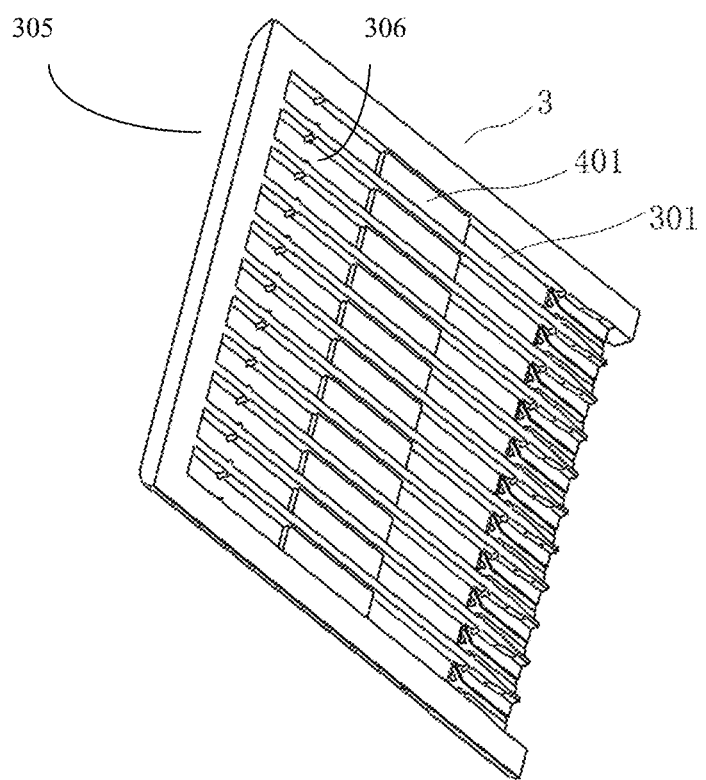
FIG. 4 depicts a stereogram of a carrier of the testing element according to an embodiment of the present invention.

A detection device comprises a collecting chamber 1, for example as shown in FIG. 1, a testing element 2, for example as shown in FIG. 3, and a carrier 3 of the testing element, for example as shown in FIG. 4 The testing element 2 has a detection area 201, and the carrier 3 of the testing element has a groove 301 for accommodating the testing element and a bump 4 is arranged in the groove 301; and the detection area is arranged on the bump 4, and the side of the detection area with test reagents (such as antibodies, chemical substances, or antigens) faces upward, the reagents contact with an analyte in the sample as to indirectly or directly detect a presence of the analyte in the sample. The height 306 of the difference in distance between the bump 4 and the depth of the groove 305 is nearly equal to or slightly smaller than the thickness of the detection area 201. The detection area is generally composed of absorbent materials. In this way, the detection area 201 is arranged on the bump 4, slightly protruding out of the surface of the carrier on the carrier. When the carrier gets close to the side wall in the collecting chamber, as the carrier presents an overall substantially plane structure and the side wall of the collecting chamber is also a substantially plane structure, the detection area contacts the inner wall of the collecting chamber, or slightly attaches to the surface of the inner wall 101 of the collecting chamber.

Figures 6A, 6B:
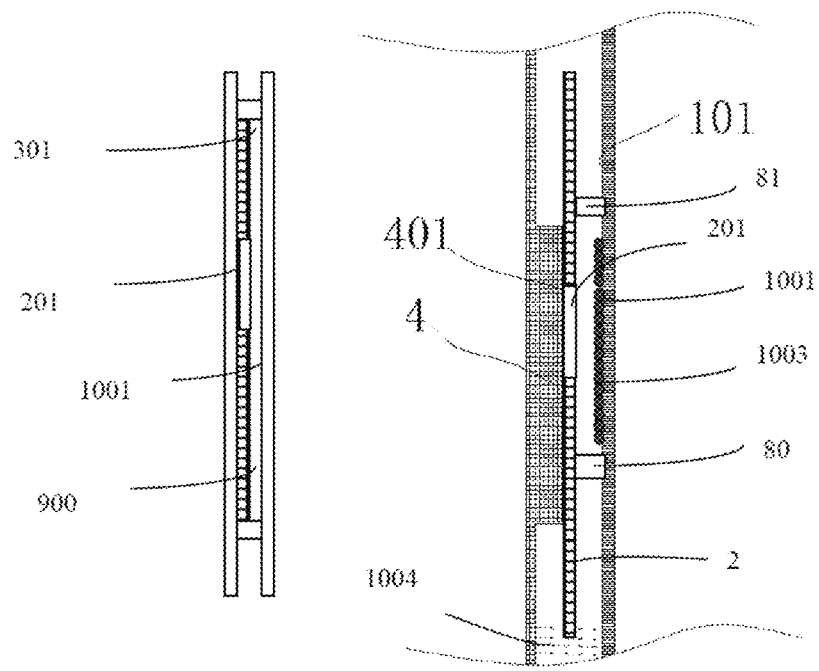
FIGS. 6A and 6B depict a schematic diagram of fitting between a bump and an inner wall of the collecting chamber according to an embodiment of the present invention.
Figure 7:
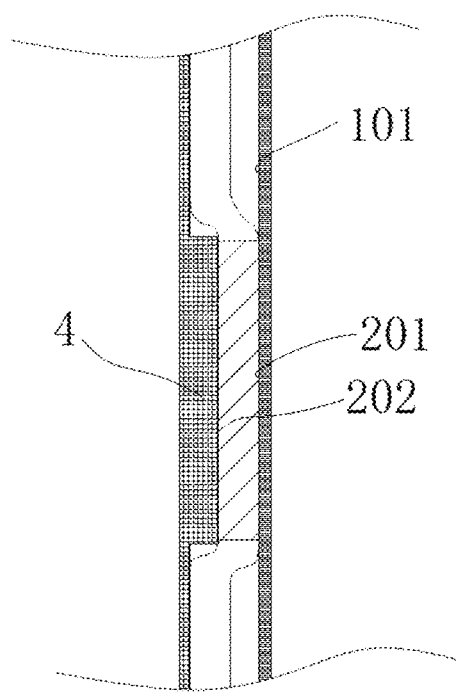
FIG. 7 depicts a schematic diagram of fitting between a bump, a detection area of the testing element and an inner wall of the collecting chamber according to an embodiment of the present invention.

In other words, when the testing element 2 on the carrier is combined with the collecting chamber 1, the detection area 201 is clamped between the bump 4 and the inner wall 101 of the collecting chamber, and the detection area 201 is attached to the inner wall 101 of the collecting chamber, for example, as shown in FIG. 6 and FIG. 7. When the testing element is installed in the collecting chamber, the inner wall of the collecting chamber covers the detection area, or covers a part of the detection area.

In some embodiments, in order to make the carrier closely contacts the side wall 101, some external pressures are applied onto the carrier to enable the detection area of the testing element on the carrier to be attached to the side wall 101 in the collecting chamber, an element 701 like an elastic element is arranged in the chamber, when the carrier is clamped between the elastic element and the inner wall 101 of the collecting chamber, the elastic element exerts a certain force on the carrier. In this way, one side 201 of the detection area is attached to or covered on the inner wall 101 of the collecting chamber, as shown in FIG. 7. Or, no space is reserved between the detection area 201 and the inside of the collecting chamber.

The inner wall 101 of the collecting chamber is transparent plastic, so that the result on the detection area is read with naked eyes through the transparent plastic, or the result of the detection area is scanned by a scanning device and saved.

When a fluid sample is collected in a collecting chamber, the collecting chamber with the testing element is generally packed in a bag containing a dry reagent and stored at a room temperature (25° C.) or at a low ambient temperature (25-30° C.), in some cold places, the ambient temperature may be below zero, for example, 5-20° C. below zero. The test device at the above temperatures is generally characterized in that the collecting chamber is made of plastic materials, and the temperature of the plastic part is also equal to or close to the ambient temperature.

When a collecting chamber device is used for testing under these temperature conditions, for example, a test subject generally collects a sample on the spot, such as urine, allowing the test subject to urine into the collecting chamber; the temperature of the urine sample is generally 35-38° C., which is higher than the ambient temperature and the temperature of the collecting chamber itself. At this time, the urine may produce water vapor or mist, when encountering with a solid material having a lower temperature than urine, it may condense into droplets on the surface of the solid material, for example, multiply-droplets water drops are covered on the solid surface. In this detection device, the detection area and the transparent inner wall 101 are closely attached with each other, so no vapor is condensed in the transparent area, and the test result on the detection area is clearly read.

Figure 5:
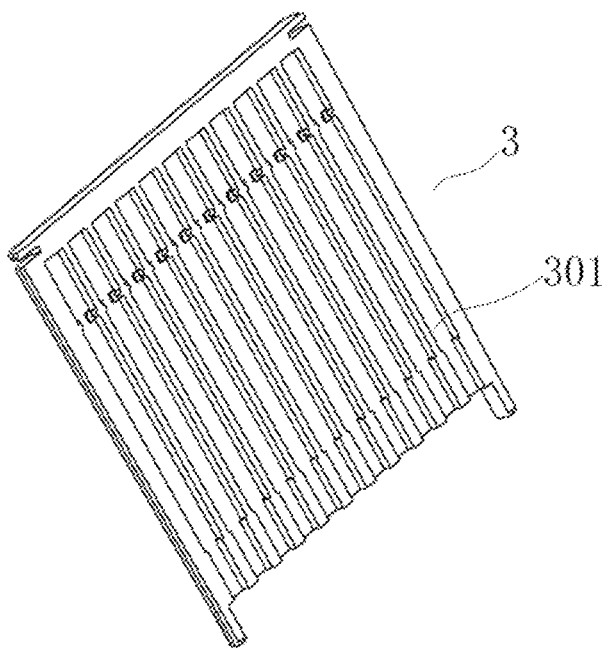
FIG. 5 depicts a stereogram of a carrier of the testing element according to another embodiment of the present invention.

On the contrary, if the detection area is not allowed to closely attach to or contact with or cover the transparent area 1001 of the side wall, but a certain distance or space is kept between them (as shown in FIG. 6A, for example, without a bump 401, a test strip is arranged in the groove, even if the groove is closely attached to the groove, there is still a certain space 900 reserved between the groove and the transparent area 1001), a water vapor that may be generated by the urine sample 1004 may condense into small droplets 1003 on the surface of the transparent area 1001 and cover on the transparent area. When the sample flows to the detection area along the testing element under the capillary action, a reaction may occur in the detection area. For example, a colored line or no colored line appears in the detection area, which indicates that the test result of the sample is a negative or positive. When a liquid covers the transparent area 1001, the detection result on the detection area on the testing element may not be read through the transparent area 1001. When the test is scanned by a scanner, due to the reflection of droplets, even if scanning is completed, the detection result may not be correctly and truly saved. In particular, when the colored line of the test result in the detection area is lighter or the color is lighter, the test on the detection area may be covered by the mists or water droplets on the transparent area 1001, thus to result in wrong reading of the result. In the embodiment, the depth of the groove of the existing traditional carrier (FIG. 5) is greater than the thickness of the testing element, arrangement of the testing element in the groove can protect the testing element from damage, but the problem proposed by the present invention is ignored.

As shown in FIG. 7, one side of the bump 4 is connected to or arranged in the groove and the other side 401 of the bump is a free face; when the testing element is combined with a collecting chamber, the free face 401 of the bump covers and attaches to the back 202 of the detection area, as shown in FIG. 6B and FIG. 7. In this way, the bump applies a pressure to the back of the detection area and presses the entire detection area against the inner wall of the collecting chamber 101, so that the inner wall of the collecting chamber fully covers and attaches to the detection area. In some embodiments, the free end face of the bump is a plane surface, a curved surface, a cylindrical surface or a conical cylindrical surface, or any other structures that enables the detection area covers or contacts or attaches to the inner wall of the collecting chamber. The attaching is actually to reduce the contact of water vapor with the inner wall of the transparent area 1001, thereby reducing the possibility of water vapor condensing into small droplets on the surface of the inner wall, and further reducing the mist.

When the testing element is combined with the collecting chamber, the distance between the free end face 401 of the bump 4 and the inner wall 101 of the collecting chamber is equal to the thickness of the detection area, for example as shown in FIG. 7. In some embodiments, when the testing element is combined with the collecting chamber, the distance between the free end face 401 of the bump and the inner wall of the collecting is less than the thickness of the detection area, so that when the testing element is installed in the collecting chamber through the carrier of the testing element, the free end face 401 of the bump 4 presses the detection area 201 against the inner wall of the collecting chamber, thus to make the detection area attaches to the inner wall of the collecting chamber. When the testing element is combined with the collecting chamber, the distance from a free end face 401 of the bump to the inner wall of the collecting chamber is greater than zero. The bump is able to make the detection area closely attaches to the inner wall 101 of the collecting chamber as a separate structure, particularly, closely attaches to the transparent area 1001.

In some embodiments, the free end face 401 of the bump may be arranged in the groove 301, for example as shown in FIG. 3. In this way, the detection area of the testing element can be wholly or partially constrained by the two side walls of the groove, so as to increase the installation stability of the testing element in the groove and makes it difficult for the testing element to withdraw from the groove. In the groove of the carrier, there may be a plurality of bumps, and each groove has its own bump, and each bump covers the back of one detection area, for example as shown in FIG. 4. In some preferred embodiments, there may be only one bump, and the bump covers the back of all the detection areas; or, there are two or more bumps, and each bump cover the back of the two or more detection areas.

Embodiment 2

Figure 2:
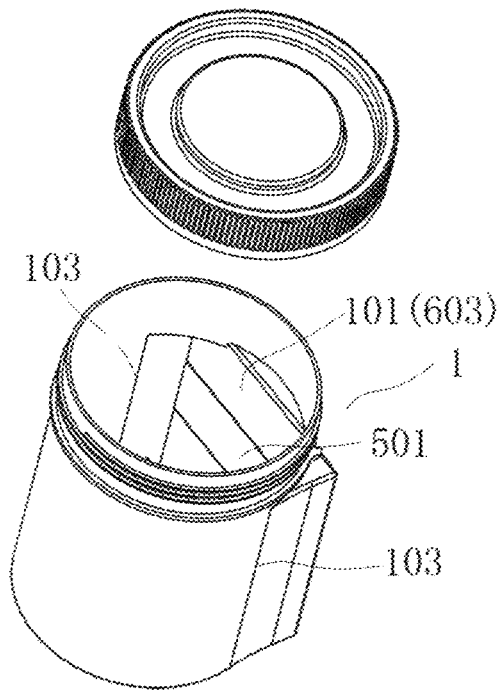
FIG. 2 depicts a stereogram of a collecting chamber according to another embodiment of the present invention.
Figure 8:
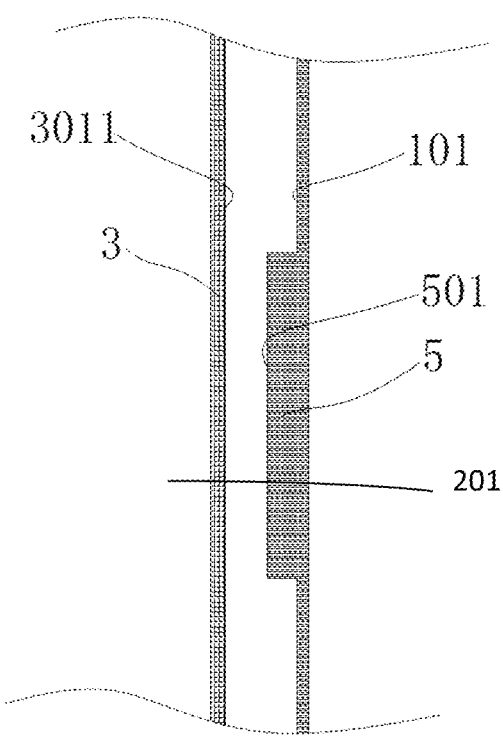
FIG. 8 depicts a schematic diagram of fitting between a carrier of the testing element and a bump according to an embodiment of the present invention.
Figure 9:
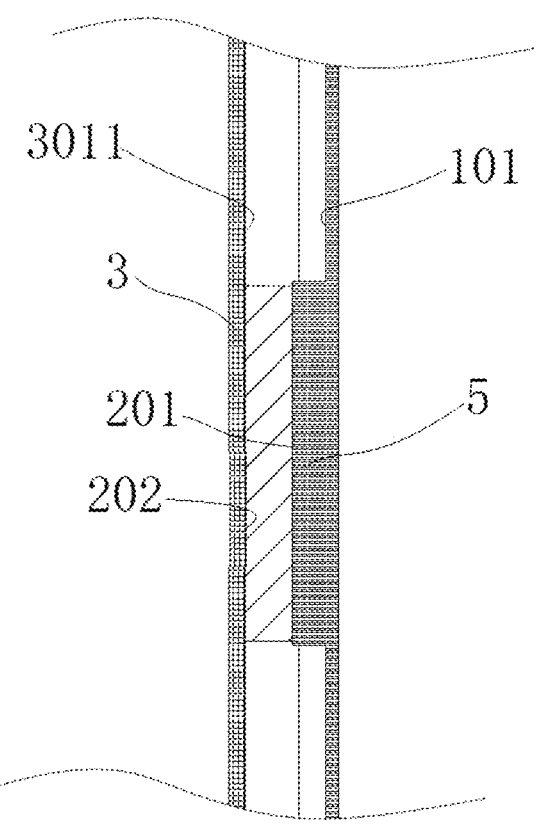
FIG. 9 depicts a schematic diagram of fitting between a carrier of the testing element, a detection area of the testing element and a bump according to an embodiment of the present invention.

A detection device comprises a collecting chamber 1, for example as shown in FIG. 2, a testing element 2, for example as shown in FIG. 3, and a carrier 3 of the testing element, for example as shown in FIG. 5; the testing element 2 has a detection area 201, and the carrier 3 of the testing element has a groove 301 for accommodating the testing element, a bulge 5 is arranged in the collecting chamber 101, when the testing element is installed in the collecting chamber, the detection area 201 is clamped between the bulge 5 and the groove 301, and the detection area is attached to the bulge, for example as shown in FIG. 8 and FIG. 9. At this time, it can be understood that the testing element is inside the groove, when the carrier gets closes to the inner wall 101 of the collecting chamber, a part of the bump 5 enters into the groove and contacts with the detection area on the testing element arranged in the groove, thereby making the detection area 201 attached to the bump 5. At this time, the bump 5 is transparent, so that the detection result on the detection area is read through the transparent side wall 101.

Similarly, one side of the bulge 5 is a connection end connected to the inner wall of the collecting chamber, and the other side 501 of the bulge is a free end; when the testing element is combined with the collecting chamber, the free end surface 501 of the bulge 5 covers and attaches to the detection area 201, for example as shown in FIG. 9. The connecting end of the bulge covers the detection area. The size of the bulge is fixed, for example as shown in FIG. 8 and FIG. 9, the bulge is a cuboid; in some embodiments, the bulge may be a cube or a cylinder. In some embodiments, the size of the bulge increases from the free end to the connecting end of the bulge, for example, the bulge is a triangular pyramid, a rectangular pyramid, or a conical-cylinder. As shown in FIG. 8, when the testing element is installed in the collecting chamber, the free end face 501 of the bulge is parallel to the bottom face 3011 of the groove. In this way, the distance between the free end face of the bulge and the bottom face of the groove is fixed. The free end face 501 of the bulge is a plane surface. In some preferred embodiments, the free end face of the bulge is a curved surface, a cylindrical surface or a conical cylindrical surface.

When the testing element is combined with a collecting chamber, the distance from a free end face 501 of the bulge to a bottom face 3011 of the groove is greater than zero. When the testing element is installed in a collecting chamber, the distance from a free end face 501 of the bulge to a bottom face of the groove 3011 is less than the thickness of the detection area 201, for example as shown in FIG. 9. In some embodiments, when the testing element is combined with the collecting chamber, the distance from a free end face of the bulge to a bottom face of the groove is equal to the thickness of the detection area. when the testing element is installed in a collecting chamber, the bulge is inserted in the groove; or the bulge is placed outside the groove. There may be one bulge, and the free end face of the bump covers and attaches to all the detection areas, for example as shown in FIG. 2; or there may be two or more bulges, the free end face of each bulge covers and attaches to one, two or more detection areas.

In some embodiments, the detection area does not necessarily cover the transparent area, when there is space reserved between the detection area and the transparent area, the detection area and the transparent area may be arranged in a relatively sealed pace to reduce the fluid flow between the space and the outside, thereby reducing the possibility of water vapor condensing on the surface of the transparent area. As shown in FIG. 6B. The detection area 201 is located above the bulge 4, but the thickness is relatively thin, and there is a gap between the detection area 201 and the collecting chamber, if there is a liquid sample, mist or small droplets may be still be formed on the inner surface of the transparent area 101, thus to cover the test result on the detection area. In order to be stay in a sealed space, a spacer structure 81, 80 may be arranged between the test strip and the side wall to make the detection area and the transparent area in a sealed area, in this way, the external water vapor, water steam or the water vapor in the air does not enter into the sealed space, which reduces the chance of water vapor condensing to water droplets on the inner surface of the transparent area 1001 in the sealed space, thereby avoiding generation of mists on the inner surface.

Figure 21:
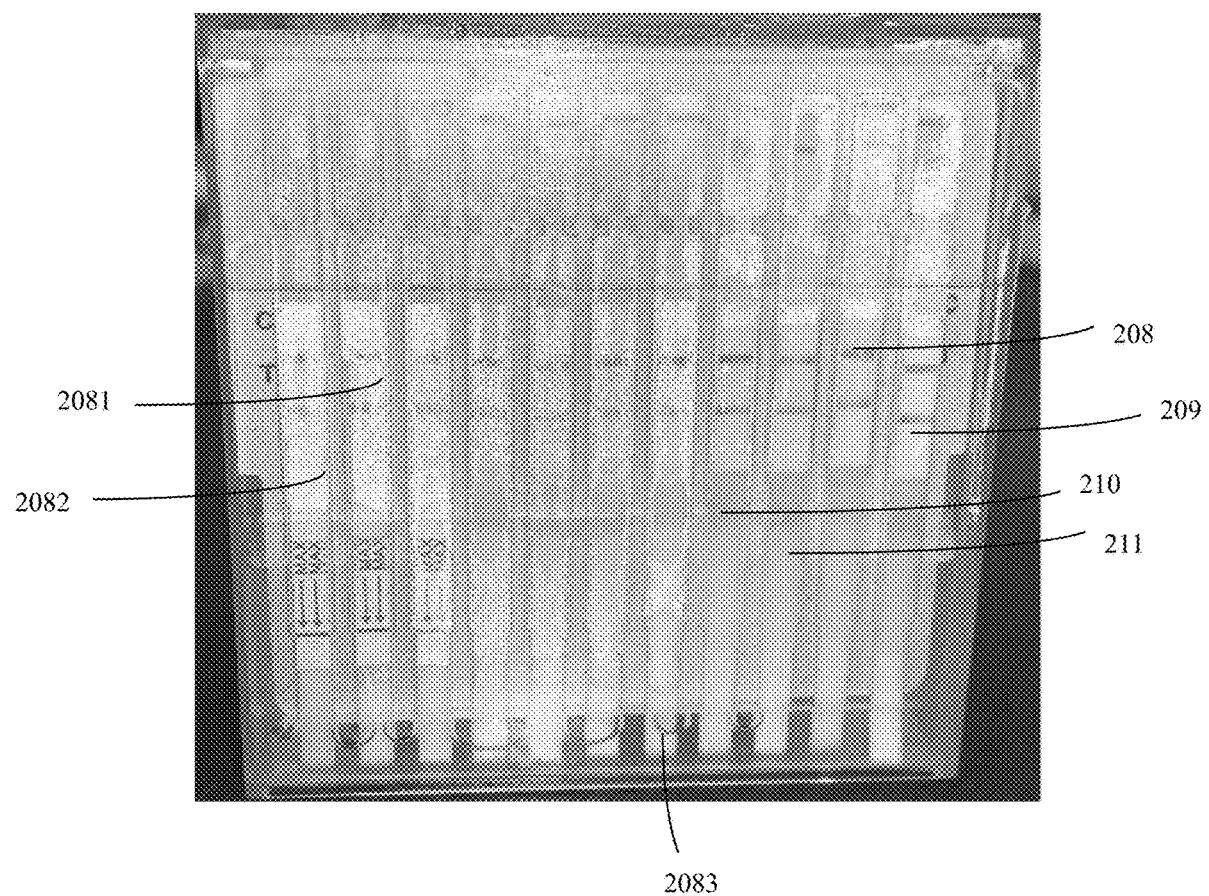
FIG. 21 depicts comparison diagram of actual product test results.

For example, as shown in FIG. 21, the left side of No. 2083 is the groove of the carrier without a bulge 4, there is distance and space between the detection area (with lines, the below is a test line, and the above is a control line of the test result) of the test strip and the transparent inner wall of the collecting chamber, and the space is not a sealed space; the right side is a groove structure (208, 209, 210, 211) with a bulge 4, the detection area contacts with the transparent area or covers on the transparent area, after a urine sample is collected and tested, on the detection area, there is micro droplets or mist on the left, which blocks the detection area, especially the test line or the control line of the detection area. While, in the area on the right, there is almost no mist or droplets condensed on the transparent inner wall, the result area is clearly visible, clearly indicating the different effects brought by different structures.

Embodiment 3

The embodiments are the combination of embodiment 1 and embodiment 2. An anti-mist detection device, comprises a collecting chamber 1, for example as shown in FIG. 2, a testing element 2, for example as shown in FIG. 3, and a carrier 3 of the testing element, for example as shown in FIG. 4; the testing element 2 has a detection area 201, and the carrier 3 of the testing element has a groove 301 for accommodating the testing element, a bump 4 is arranged in the groove 301, and a bulge 5 is arranged on the inner wall of the collecting chamber; when the testing element 2 is combined with the collecting chamber 1, the bulge 5 is arranged facing the bump 4 and the detection area 201 is arranged between the bulge 5 and the bump 4, and the detection area 201 is attached to the bulge 5, for example as shown in FIG. 10 and FIG. 11.

Figure 10:
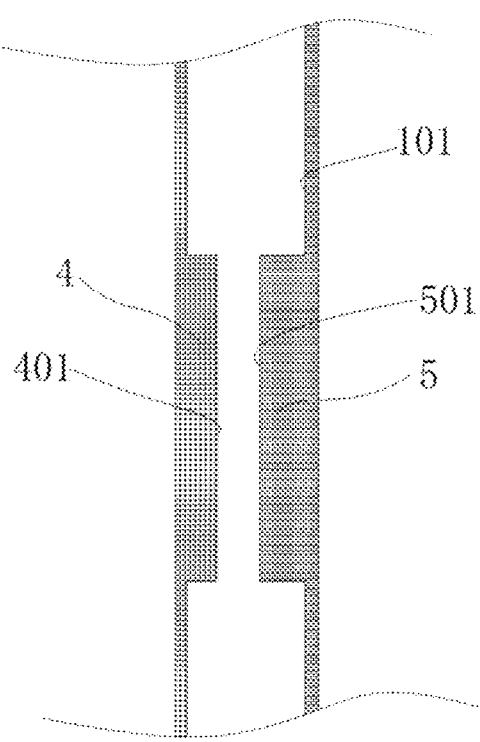
FIG. 10 depicts a schematic diagram of fitting between a bump and a bulge according to an embodiment of the present invention.
Figure 11:
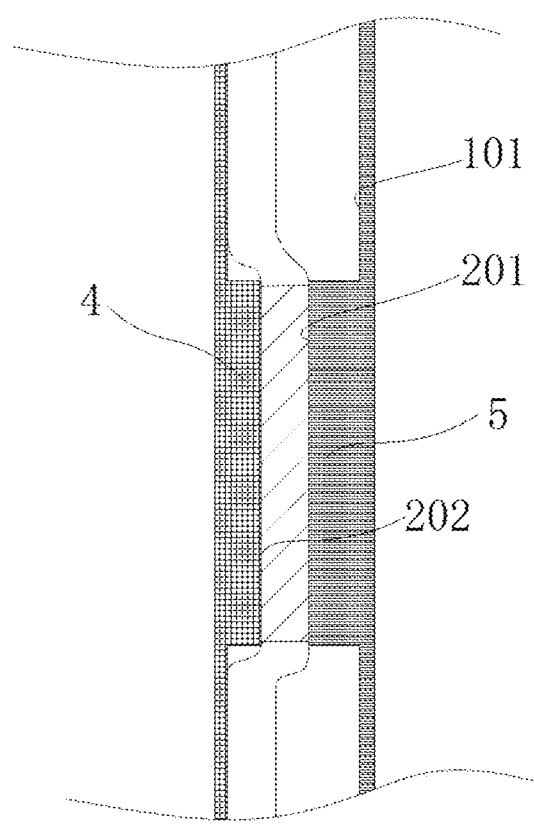
FIG. 11 depicts a schematic diagram of fitting between a bump, a detection area of the testing element and a bulge according to an embodiment of the present invention.

One side of the bump 4 is connected to the groove, and the other side of the bump 4 is a free end 401; when the testing element 2 is combined with a collecting chamber 1, the free end face 401 of the bump covers and attaches to the back of the detection area 201, as shown in FIG. 10 and FIG. 11. The free end face of the bump is located inside the groove, for example as shown in FIG. 4.

Embodiment 4

Figure 13:
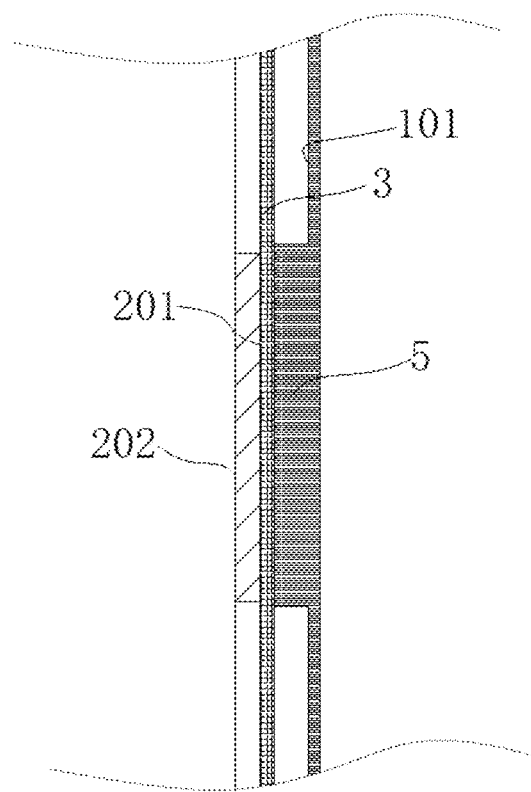
FIG. 13 depicts a schematic diagram of fitting between, a detection area of the testing element, a carrier of the testing element and a bump according to an embodiment of the present invention.

In some embodiments, the present inventions provides a detection device, comprising a collecting chamber 1, for example as shown in FIG. 2, a testing element 2, for example as shown in FIG. 3, and a carrier 3 of the testing element, for example as shown in FIG. 5; the testing element 2 has a detection area 201. When the testing element 2 is combined with the collecting chamber 1, the carrier 3 of the testing element is clamped between the detection area 201 and the inner wall 101 of the collecting chamber, that is, the detection area 201 for displaying the detection result contacts the bottom of the groove of the carrier, and the back of the detection area 202 extends out of the groove, so that the detection area attaches to the bottom of the groove of the carrier and gets close to the carrier of the testing element 3 relative to the back 202 of the detection area, for example as shown in FIG. 13. That is, in this embodiment, the blocking element is a carrier of the testing element, and the testing element is located between the carrier and the side wall of the collecting chamber. The carrier of the testing element is made of transparent material. In some embodiments, the carrier of the testing element is made of a semi-transparent material, so the carrier corresponding to the detection area is transparent, and the side wall or the bulge 5 of the collecting chamber is also transparent, in this way, the result in the detection area 201 on the testing element is read through the transparent area. According to the structure as shown in FIG. 13, the detection area contacts with the bottom of the groove of the carrier, and the carrier is in close contact with the bulge 5, so that external water vapor or water steam may not condense on the surface of the bulge 5 contacting the carrier, no droplets may be generated on the contact surface of the detection area with the carrier, thus avoiding a misted interface.

Figure 12:
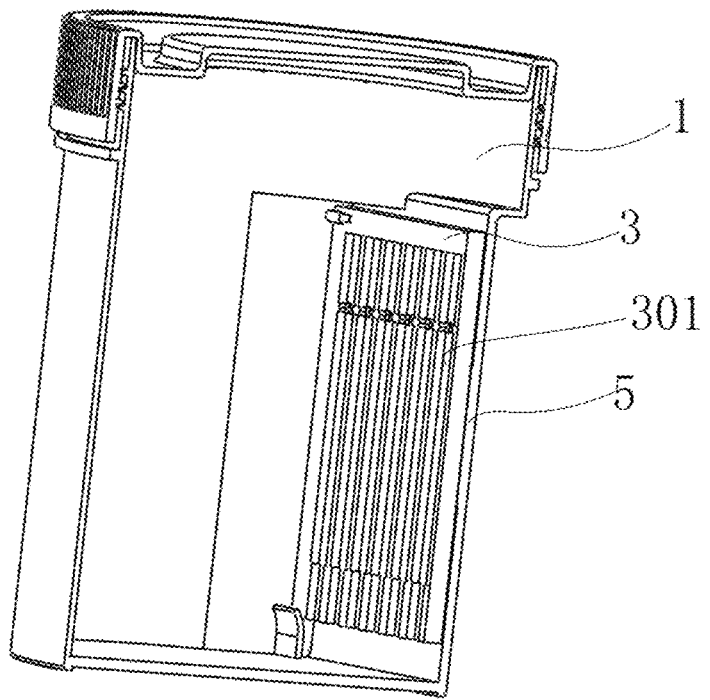
FIG. 12 depicts a stereogram of fitting between a bump and a back of the carrier of the testing element according to an embodiment of the present invention.

In some embodiments, the carrier of the testing element carrier is respectively connected to the testing element and to the inner wall of the collecting chamber detachably. In some embodiments, the carrier of the testing element may be fixedly connected to the testing element. When the testing element 2 is installed on the carrier 3 of the testing element, the carrier 3 of the testing element covers and attaches to the detection area 201; when the testing element 2 is combined with the collecting chamber 1, the carrier 3 of the testing element attaches to the inner wall 101 of the collecting chamber, for example as shown in FIGS. 12 and 13. In this way, the carrier of the testing element fills out the area between the detection area and the inner wall of the collection chamber as possible.

In some embodiments, the inner wall of the collecting chamber has a protrusion for attaching to the carrier of the testing element, for example as shown in FIGS. 2 and 13, one side of the bulge 5 is a connection end connected to the inner wall of the collecting chamber, and the other side of the bulge is a free end; when the testing element 2 is combined with the collecting chamber 1, the free end surface 501 of the bulge 5 covers on and attaches to the detection area 201. In this embodiment, the carrier of the testing element is arranged between the bulge and the detection area, and when the bulge covers the detection area, it directly contacts with the detection area. The size of the bulge is fixed, for example as shown in FIG. 2 and FIG. 13, the bulge is a cuboid; in some embodiments, the bulge may be a cube or a cylinder. In some embodiments, the size of the bulge increases from the free end to the connecting end of the bulge, for example, the bulge is a triangular pyramid, a rectangular pyramid, or a conical-cylinder.

The carrier of the testing element has a mounting surface, and the mounting surface has a groove 301 for accommodating the testing element; when the testing element is installed on the carrier of the testing element, the bottom face of the groove covers and attaches to the detection area; when the testing element is combined with the collecting chamber, the back of the mounting surface attaches to the inner wall of the collecting chamber, and the distance between the bottom face of the groove and the mounting surface is fixed.

Embodiment 5

The present inventions provides a collection and detection device with a detection chamber, for example as shown in FIGS. 2, 14, 17 and 18, comprising a collecting chamber 1, the collecting chamber has an opening 102, the detection chamber 6 is located below the opening 102, and the detection chamber 6 is a chamber formed by the inner wall of the collecting chamber protruding outward, a side wall of the collecting chamber has two connections 103 to the detection chamber, and a lateral dimension of the detection chamber 6 is greater than or equal to a lateral distance between the two connections 103. In this way, the testing element is inserted into the detection chamber through the connections between the collecting chamber and the detection chamber and installed in the detection chamber. Two connections 103 to the detection chamber are symmetrical to the axis of the collecting chamber 1; the detection chamber 6 is symmetrical to the axis of the collecting chamber 1, as shown in FIG. 16 or FIG. 20.

Figure 16:
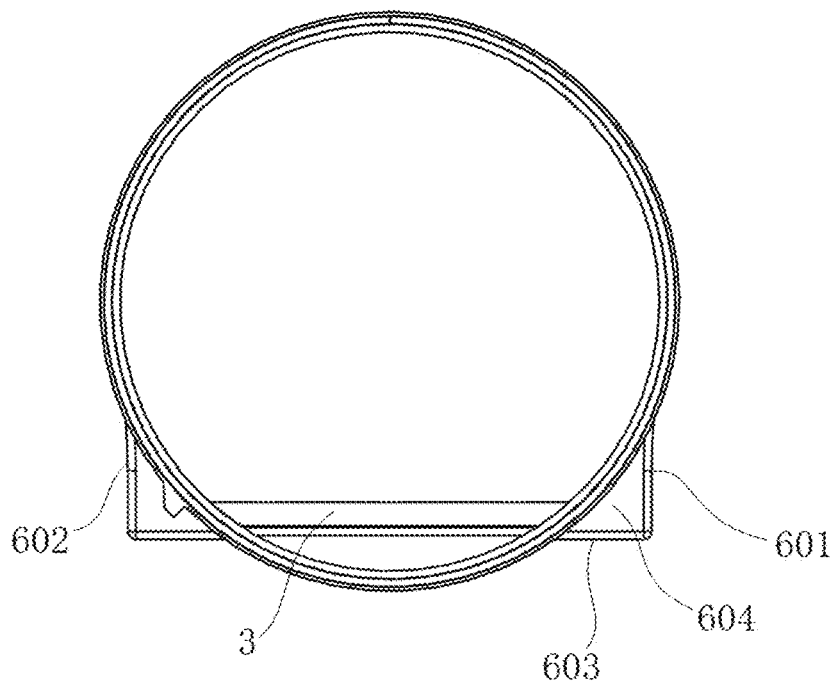
FIG. 16 depicts a top view of a collecting chamber according to FIG. 2.
Figure 20:
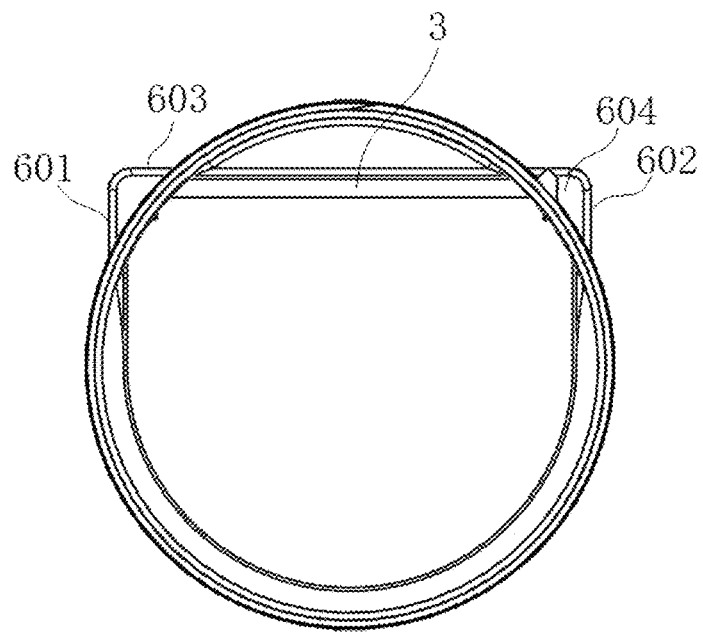
FIG. 20 depicts a top view of a collecting chamber according to FIG. 17.

The lateral dimension of the detection chamber 6 is fixed, as shown in FIG. 16 or FIG. 20. In some embodiments, the lateral dimension of the detection chamber gradually extends outward from the connections. When the lateral dimension of the detection chamber gradually extends outward from the connections, the lateral dimension of the detections chamber is the smallest at the connection to the collecting chamber.

The detection chamber 6 has a first side wall 601 and a second side wall 602 respectively connected to the two connections, the first side wall 601 and the second side wall 602 are parallel with each other, as shown in FIG. 16 or FIG. 20. In some embodiments, the first side wall and the second side wall are intersected, so that the lateral dimension of the detection chamber gradually extends outward from the connections. Both the first side wall and the second side wall are plane. The first side wall and the second side wall are parallel to the axis of the collecting chamber.

Figure 17:
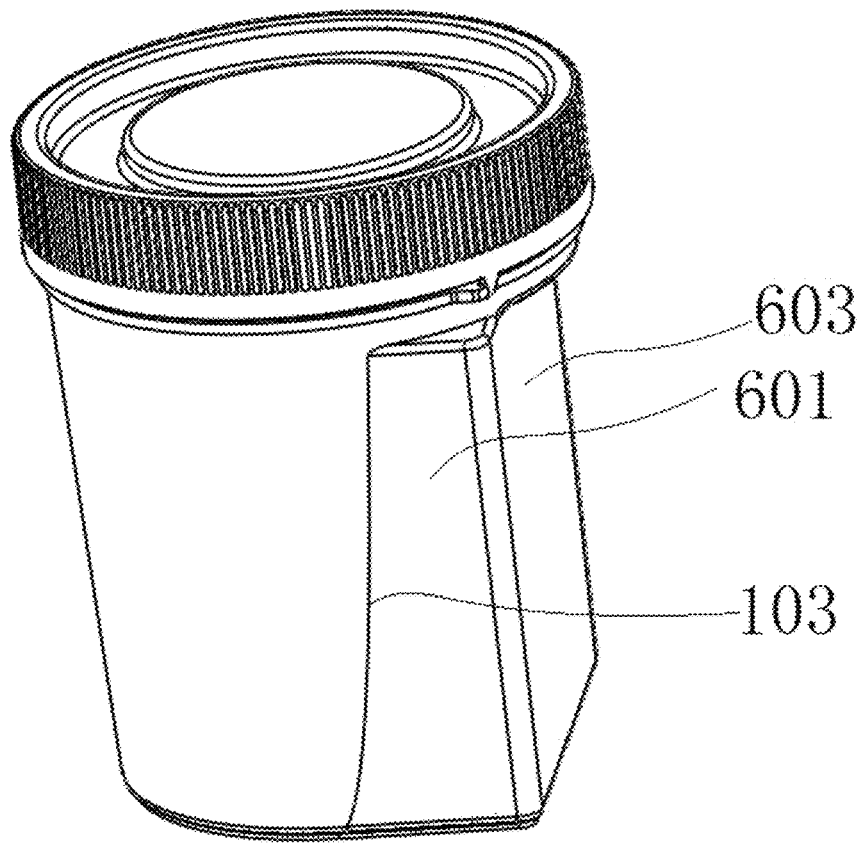
FIG. 17 depicts a stereogram of another collecting chamber

The detection chamber 6 has a third side wall 603 for connecting a first inner wall 601 with a second inner wall 602, the third side wall 603 is close to the middle part of the collecting chamber relative to an opening 102 of the collecting chamber, as shown in FIG. 2 or FIG. 17. The third side wall 603 is plane. The third side wall 603 is parallel to the axis of the collecting chamber.

The detection chamber 6 has a top face 604, and the top face 604 is connected to the side wall of the collecting chamber and the top face 604 is located at an outer edge of the opening of the collecting chamber, as shown in FIG. 16 or FIG. 20. The top face 604 is plane. The top face 604 is perpendicular to the axis of the collecting chamber.

Figure 14:
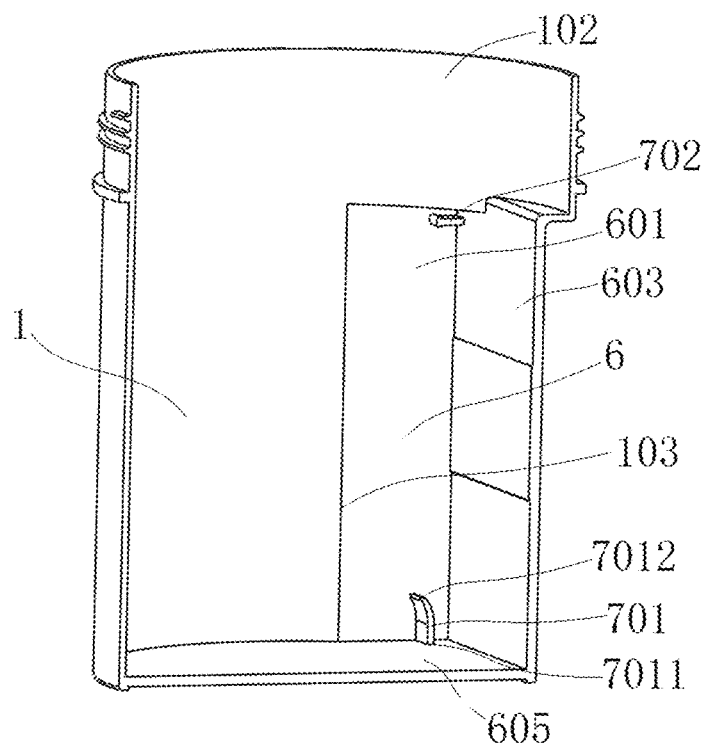
FIG. 14 depicts a transverse section diagram of a collecting chamber according to FIG. 2.
Figure 15:
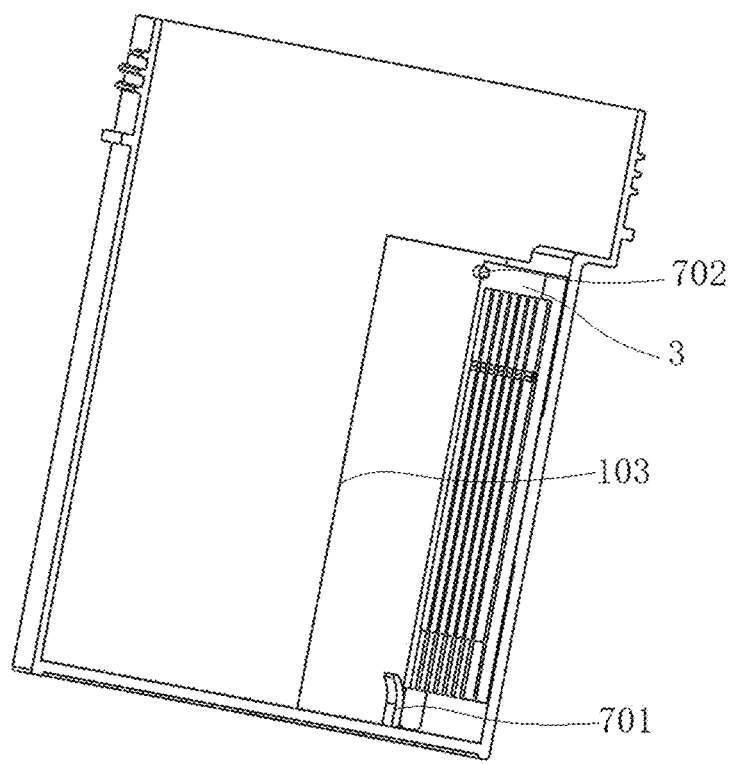
FIG. 15 depicts an assembly diagram of a collecting chamber and a carrier of the testing element according to FIG. 2.
Figure 18:
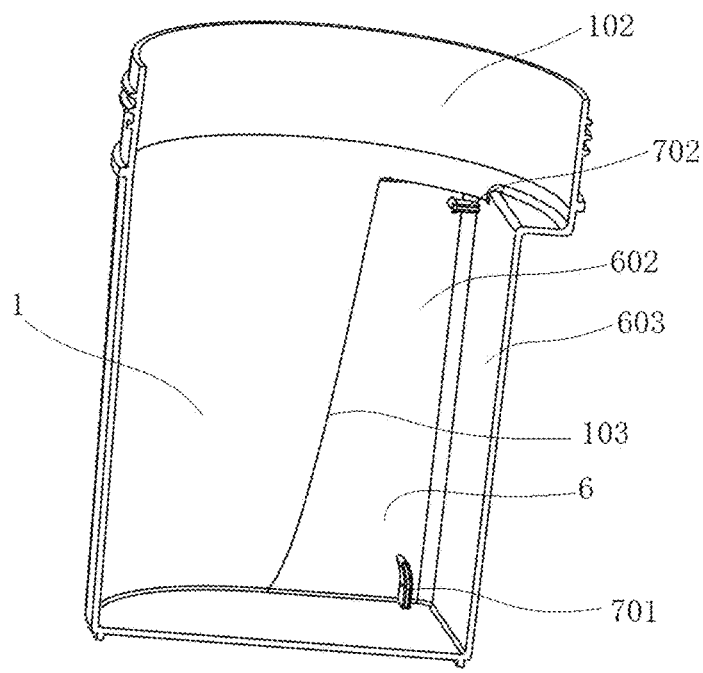
FIG. 18 depicts a transverse section diagram of a collecting chamber according to FIG. 17.
Figure 19:
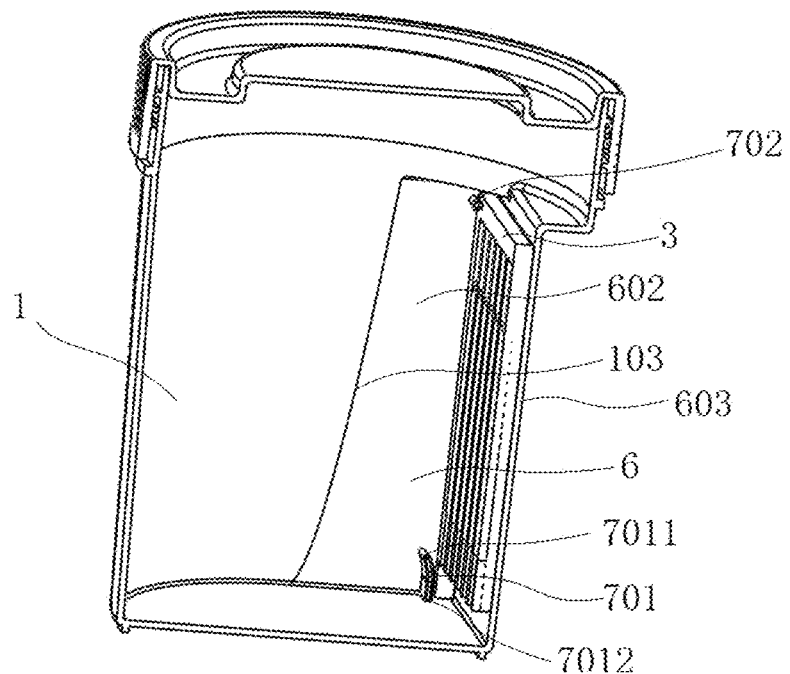
FIG. 19 depicts an assembly diagram of a collecting chamber and a carrier of the testing element according to FIG. 17.

The detection chamber 6 has a bottom face 605, and the bottom face 605 is in the same plane as the bottom face of the collecting chamber, as shown in FIG. 14 or FIG. 18. The bottom face 605 is parallel to the top face 604.

As shown in FIGS. 14, 5 or FIGS. 18 and 19, the detection chamber 6 has a locking structure, and the locking structure comprises a locating element 701, wherein one end of the locating element 701 is a connection end 7011 connected to the bottom face of the detection chamber and the other end of the locating element is a free end 7012, the free end 7012 of the locating element is close to the middle of the collecting chamber relative to the connection end 7011 of the locating element. The locating element 701 is close to the third side wall 603. The locking structure further comprises a clamping element 702, and the clamping element 702 protrudes out of the third side wall 603. The carrier 3 of the testing element has a groove or a straight slot for fitting with the clamping element; when the testing element is installed in the detection chamber, the clamping element is inserted into the groove to achieve installation and fixing of the testing element. The clamping element 702 is close to the top of the third side wall 603. In this way, the locating element fixes a lower side of the testing element; the clamping element fits with the groove of the testing element to achieve fixing of an upper side of the testing element.

The content described in the embodiments of the specification is merely an illustration of the implementation embodiments of the present invention, the protection scope of the present invention is not regarded as limited to the specific embodiments described in the embodiments, and the protection scope of the present invention also cover the equivalent techniques in the art Equivalent technical means conceivable by the technicians in the field according to the present invention.

What is claimed is:

1. A detection device comprising: a testing element and a transparent area, wherein the testing element comprises a detection area which is configured to detect a presence of an analyte in a liquid sample; the transparent area is configured to have a test result on the detection area to be read through the transparent area; a part of the transparent area contacts a part of the detection area, or the detection area and the transparent area are arranged in a sealed space, thus to make a fluid in the sealed space not exchange with a fluid outside the sealed space, wherein the detection device comprises a chamber used for collecting the liquid sample and a blocking element, the blocking element is configured to reduce or block fluid exchange between the detection area and an inner wall of the chamber and surrounding so that a liquid substance originating from the liquid sample cannot enter into an area between the detection area and the inner wall of the chamber therefore avoiding mist that could affect reading the result on the detection area.

2. The detection device of claim 1, wherein the detection area comprises a side for displaying the test result and a back side, the transparent area comprises a side facing the detection area, the side for displaying the test result contacts the side of the transparent area facing the detection area; or the side for displaying the test result covers the side of the transparent area facing the detection area.

3. The detection device of claim 2, wherein the detection area indicates the test result by color changes.

4. The detection device of claim 2, wherein the chamber comprises a side wall, and the transparent area is arranged on the side wall.

5. The detection device of claim 4, wherein the detection device is used to contain a carrier of the testing element, the carrier comprises a groove, and the testing element is arranged in the groove.

6. The detection device of claim 5, wherein the blocking element makes the detection area of the testing element closely adhere to a surface of the transparent area.

7. The detection device of claim 5, wherein the blocking element makes the detection area and the transparent remain in the sealed space.

8. The detection device of claim 6, wherein the blocking element is arranged in the groove of the carrier, the blocking element comprises a side that contacts the back side of the detection area, and when the carrier is combined with the chamber, the blocking element makes the detection area adhere to the transparent area on the side wall.

9. The detection device of claim 6, wherein the blocking element is arranged in the groove of the carrier, so that when the carrier is combined with the chamber, the blocking element makes the detection area adhere to one side of the transparent area, and the blocking element is transparent.

10. The detection device of claim 4, wherein the transparent area adopts a plane structure.

11. The detection device of claim 8, wherein the blocking element presents a raised structure, and the raised structure comprises a side that contacts the back side of the detection area; when the carrier is combined with the chamber, the distance between the side of the raised structure contacting the back side of the detection area and the surface of the transparent area is less than or equal to the thickness of the detection area.

12. The detection device of claim 2, wherein the detection area comprises a porous absorbent material.

13. The detection device of claim 12, wherein the porous absorbent material comprises a nitrocellulose film or a nylon thin film.

14. The detection device of claim 12, wherein the detection area comprises a test line and a control line, wherein a color appearance or shade in the test line suggests the presence or the quantity of the analyte.

15. The detection device of claim 1, wherein the test result in the detection area is configured to be read by naked eyes or an electronic device.

16. The detection device of claim 15, wherein the electronic device is an electronic scanner.

17. The detection device of claim 1, wherein the fluid in the sealed space comprises a gas containing water vapor.

18. The detection device of claim 1, wherein the liquid sample is a urine sample.

19. The detection device of claim 1, wherein the analyte comprises a substance of drugs.

20. The detection device of claim 1, wherein the transparent area is formed by transparent non-absorbent materials.

* * * * *